(12) United States Patent
Van Hasselt et al.

(10) Patent No.: US 10,356,535 B2
(45) Date of Patent: Jul. 16, 2019

(54) METHOD AND SYSTEM FOR SELF-MANAGED SOUND ENHANCEMENT

(71) Applicant: ACE Communications Limited, Hong Kong (HK)

(72) Inventors: Charles Andrew Van Hasselt, Hong Kong (HK); Pui Tong Paul Lee, Hong Kong (HK); Chi Shan Anna Kam, Hong Kong (HK); Ka Kui Cheng, Hong Kong (HK)

(73) Assignee: ACE Communications Limited, Hong Kong (HK)

( * ) Notice: Subject to any disclaimer, the term of this patent is extended or adjusted under 35 U.S.C. 154(b) by 0 days.

(21) Appl. No.: 15/727,639

(22) Filed: Oct. 9, 2017

(65) Prior Publication Data

US 2018/0035216 A1 Feb. 1, 2018

Related U.S. Application Data

(63) Continuation of application No. 15/296,028, filed on Oct. 17, 2016, now Pat. No. 9,782,131, which is a (Continued)

(51) Int. Cl.
*H04R 25/00* (2006.01)
*A61B 5/00* (2006.01)
(Continued)

(52) U.S. Cl.
CPC ......... *H04R 25/505* (2013.01); *A61B 5/0022* (2013.01); *A61B 5/121* (2013.01);
(Continued)

(58) Field of Classification Search
CPC .... H04R 25/30; H04R 25/305; H04R 25/505; H04R 25/558; H04R 25/70;
(Continued)

(56) References Cited

U.S. PATENT DOCUMENTS

| 4,759,070 | A  | * | 7/1988 | Voroba | A61B 5/12 |
| | | | | | 381/328 |
| 7,564,979 | B2 | * | 7/2009 | Swartz | A61B 5/121 |
| | | | | | 381/312 |
| 2010/0119093 | A1 | * | 5/2010 | Uzuanis | H04R 25/70 |
| | | | | | 381/312 |

* cited by examiner

*Primary Examiner* — Huyen D Le
(74) *Attorney, Agent, or Firm* — Idea Intellectual Limited; Margaret A. Burke; Sam T. Yip

(57) ABSTRACT

A system for capturing an individual's hearing characteristics, including loudness tolerance levels at different sound frequencies, as an individualized shaped auditory profile for automatically enhancing audio to complement and address an individual's hearing deficits experienced via a particular signal pathway including the audio device, the sound environment, and the individual's hearing capabilities. The auditory profile is used to produce enhanced sound subsequently transmitted to the individual via the same signal pathway. The enhanced sound may be produced with consideration of both ears' auditory profile shapes together to increase the dynamic range of the enhanced sound. The sound enhancement can be introduced gradually over a sound reproduction session or a period of time of use. Manual gain adjustments applied by multiple users to particular sound enhancement are recorded and used in pattern recognition to allow the system to learn and suggest alternatives to the desired sound enhancement for the auditory profile.

8 Claims, 28 Drawing Sheets

Related U.S. Application Data continuation-in-part of application No. 14/151,375, filed on Jan. 9, 2014, now Pat. No. 9,468,401, which is a continuation-in-part of application No. 13/184,776, filed on Jul. 18, 2011, now Pat. No. 9,138,178.

(60) Provisional application No. 61/750,779, filed on Jan. 9, 2013, provisional application No. 61/371,068, filed on Aug. 5, 2010, provisional application No. 61/379,237, filed on Sep. 1, 2010.

(51) Int. Cl.
*A61B 5/12* (2006.01)
*G06F 19/00* (2018.01)
*G16H 40/67* (2018.01)
*H04R 5/04* (2006.01)

(52) U.S. Cl.
CPC ............ *A61B 5/123* (2013.01); *A61B 5/128* (2013.01); *A61B 5/6898* (2013.01); *G06F 19/00* (2013.01); *G16H 40/67* (2018.01); *H04R 25/70* (2013.01); *H04R 5/04* (2013.01); *H04R 25/305* (2013.01); *H04R 25/75* (2013.01); *H04R 2205/041* (2013.01); *H04R 2225/39* (2013.01); *H04R 2225/41* (2013.01); *H04R 2225/55* (2013.01); *H04R 2430/01* (2013.01); *H04R 2460/01* (2013.01); *H04R 2460/07* (2013.01)

(58) Field of Classification Search
CPC ............ H04R 2225/39; H04R 2225/41; H04R 2430/01; A61B 5/12; A61B 5/121
USPC ..... 381/56, 58, 60, 312, 314, 315, 320, 321, 381/71.6, 104; 73/585
See application file for complete search history.

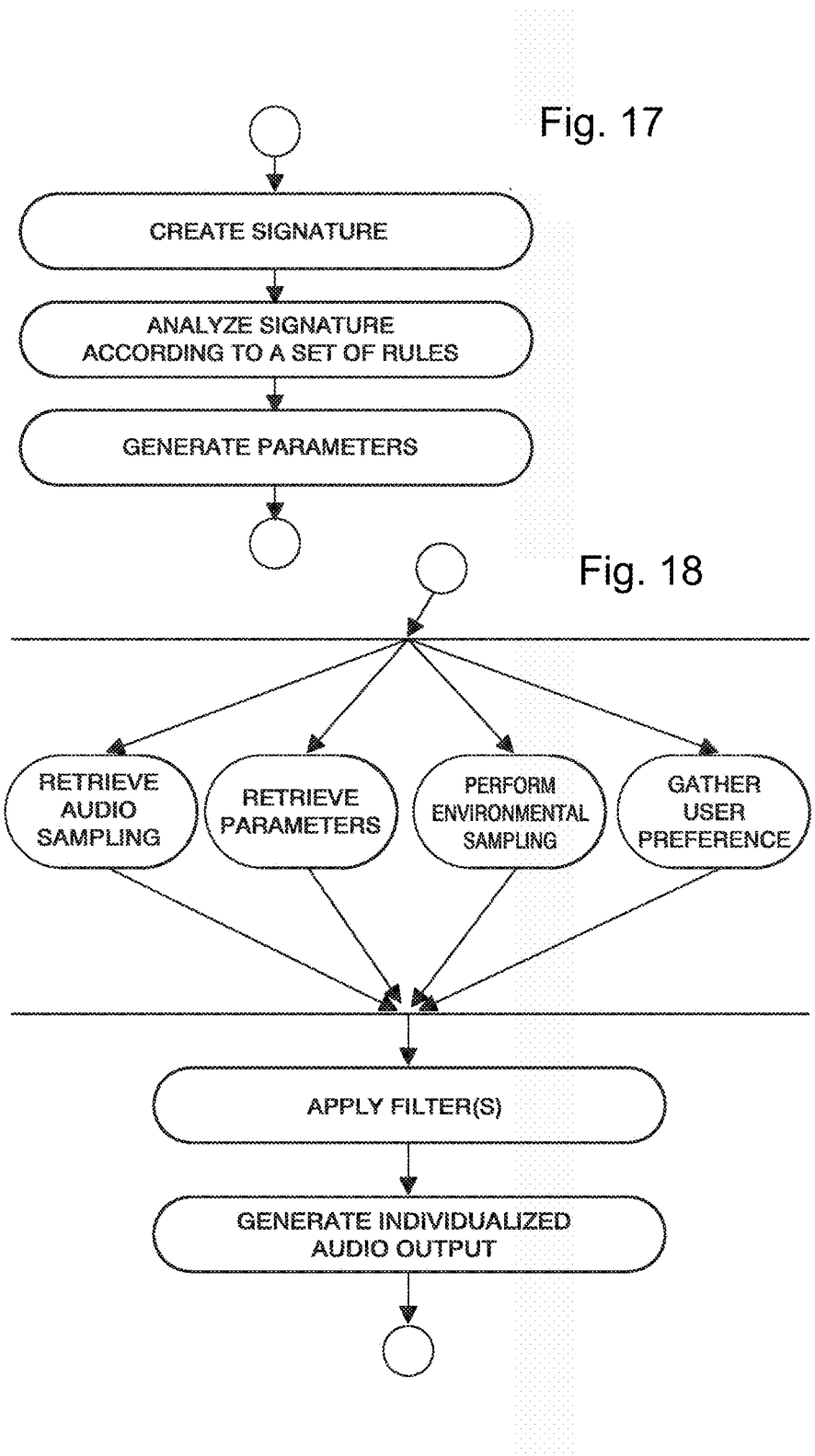

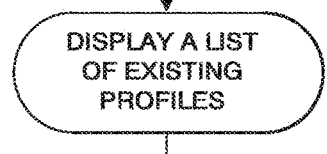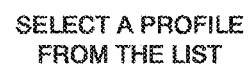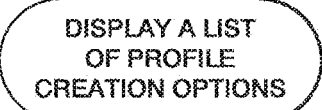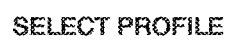
Fig. 24
Fig. 25

METHOD AND SYSTEM FOR SELF-MANAGED SOUND ENHANCEMENT

CROSS-REFERENCES TO RELATED APPLICATIONS

This application is a continuation-in-part of U.S. patent application Ser. No. 15/296,028 filed Oct. 17, 2016, which is a continuation of U.S. patent application Ser. No. 14/151,375 filed Jan. 9, 2014, which in turn claims the benefit of U.S. patent application Ser. No. 61/750,779 filed Jan. 9, 2013, and is a continuation-in-part of U.S. patent application Ser. No. 13/184,776 filed Jul. 26, 2012, which in turn claims the benefit of U.S. patent application Ser. No. 61/371,068 filed Aug. 5, 2010, and U.S. patent application Ser. No. 61/379,237 filed Sep. 1, 2010, the disclosures of which are incorporated herein by reference in their entirety.

BACKGROUND

This invention is directed in general to the field of audiology and digital sound engineering and in particular to a system and method for enhancing user experience based on an individualized audiological profile.

Hearing loss has been estimated to be the most prevalent disability in developed countries. Literally millions of people worldwide suffer from hearing disabilities, many of whom are unaware of their hearing loss. The decreased hearing capability may be due to several factors, including age, health, occupation, injury and disease. The loss of hearing can lead to significant reductions in quality of life, impaired relationships, reduced access to employment and diminished productivity. Different types of hearing loss and related conditions can affect people's daily activities in different ways, in particular having phone conversations and listening to music.

In general, hearing sensitivity to high-pitched sound tends to lessen first. People generally are not aware of the decrease in their hearing sensitivities until they experience hearing problems, for instance, difficulty understanding a conversation on the phone or having problems hearing in a noisy environment. For people with hearing deterioration, their hearing capabilities are generally sufficient for most listening situations. Since the impact of their hearing loss is tolerable, they tend to ignore or find a way around it. They might avoid talking on the phone in noisy environments and would unlikely seek help from a hearing healthcare professional. Individuals with significant hearing loss may consult a hearing healthcare professional to be prescribed and procure a hearing aid. Although wearing a hearing aid is considered as one of the less intrusive assistive technologies for hearing loss patients, it is not without problems. To use a hearing aid during a phone conversation or music enjoyment via headphones is clumsy and inconvenient. People using a hearing aid often experience feedback, the squeal created by the hearing aid output sound being picked up by the hearing aid microphone.

A common problem associated with hearing loss is tinnitus. Tinnitus is a conscious experience of sound that originates in the head (i.e., without an external acoustic source) and may be manifest by an evident audible ringing that interferes with other sounds around one or more frequencies. Tinnitus is a common condition and a symptom normally observed with age-related hearing loss. Tinnitus is known to affect individuals to varying degrees and in a great number of different ways. Some people with chronic tinnitus are able to ignore the condition while others find it annoying, intrusive, distracting, and even disabling. Tinnitus may interfere with sleep, causing both emotional distress and other ill-effects on general health.

Many tinnitus sufferers notice that their tinnitus changes in different acoustic surroundings; typically, it is more bothersome in silence and less annoying in sound-enriched environments. This phenomenon has led to the development of sound therapies for tinnitus treatment. The most common recommendation is to "avoid silence" by enriching the background sounds. This can be accomplished by simply playing some background sound or music. More sophisticated sound therapies involve measuring the pitch and loudness of the tinnitus signals and providing signals which can be played via ear level devices and sound generators.

One of the aspects of the invention is hearing profiling, particularly through self-administered testing. During hearing profiling, minimum audible hearing levels for a set of audiometric frequencies are measured. Various methods are known for obtaining minimum audible hearing levels. During application of hearing profiling to a hearing enhancement device (such as a hearing aid, sound amplifier, or personal listening device such as an MP3 player, a smart phone or the like) in a specific situation, however, a person at times may insist on increasing or decreasing device volume in order to sufficiently hear and comprehend otherwise enhanced audio as determined by hearing tests and corresponding modification of the hearing profile at the ear as part of the sound enhancement process. One problem is that the unintentional induced loudness in the enhanced audio may cause hearing discomfort and damage. A person may have a higher tolerance level for a certain audiometric frequency while having a lower tolerance level for another frequency. A person's sound loudness tolerance profile differs from person to person. The difference may not be very significant among people with normal hearing. However, it is not the case for people with various degrees of hearing impairments, such as hearing loss, tinnitus, and hearing loss with tinnitus. Due to the difference in people's sound loudness tolerance profiles, the hearing curve of a person with normal hearing should not be used as the standard. Thus, fitting of a person's hearing curve without taking into consideration the person's sound loudness tolerance profile may lead to hearing discomfort or damage.

Simply increasing device volume in order to sufficiently hear and comprehend enhanced audio as governed by the sound enhancement process may be dangerous. Increasing or decreasing device volume implies amplifying or de-amplifying audio of all audiometric frequencies by the same factor. A person typically requires amplifying or de-amplifying a limited range of audiometric frequencies. Increasing or decreasing the loudness of audio of all audiometric frequencies may lead to a range of hearing problems. A system capable of handling the various sound loudness tolerance profiles with various degrees of hearing impairments is needed. More specifically, solutions to the problems identified herein, such as hearing difficulties during phone conversations or while listening to music, as well as feedback created by use of a hearing aid, are needed.

Conventional "hearing tests" require a calibrated device to measure the hearing threshold level of an individual in a quiet environment. The data set captured from such hearing tests thus represents the threshold values of an individual's hearing.

In order for a device to produce a specific sound wave amplitude as a test tone, the device and its transducer combination require calibration. The reason for this is that the circuitry and transducer or earphone of each device have different frequency responses that influence the output amplitude of sound waves. This means the same electric audio signal will result in different amplitudes of sound waves for devices and earphones of different models. Therefore, by calibrating the device and the earphone combination, specific sound wave amplitudes as test tones can be produced for hearing testing purposes.

By using a calibrated device, consistent sound wave amplitudes can be produced and the accurate value of hearing levels can then be obtained by finding the thresholds over a range of frequencies in a sound-proof or quiet environment, and producing a "hearing profile" which will represent a subject's hearing threshold or audiogram. The inventors' work on this aspect has been published in The International Journal of Audiology Vol. 51, No. 8, p 606-610 (August 2012). The data thus captured within the device may then be used as parameters based upon which the signal processing engine can modify or enhance the audio signal.

During development, experiments were carried out and results from individuals with "normal" hearing and individuals with hearing loss over a range of frequencies revealed there are factors which are important and should be taken into account during audio signal enhancement. Among these factors are transducers in the earphones and environmental noise. Further investigation using various earphones which differ from the calibrated (standard) earphone confirmed the importance of the "transducer effect." Indeed, any electronic component, whether substituted for another component or added to/removed from a calibrated signal pathway may contribute to the transducer effect. For example, the inventors have found that even two units of the same Samsung Galaxy Tab® model, but made in different years and bearing different sound cards, can have slightly different audio properties.

It was found that using different earphones, the same user's profiles obtained could differ slightly between the various models of earphones. The differences are due to the different frequency responses of the earphone's transducer compared with the transducer of the earphone for which the system was calibrated.

During development, experiments were carried out that revealed that background environment noise also affects the individual abilities to perceive or understand the acoustic signals. This is due to the "masking effect" of the background noise. If the environment noise is analyzed and then taken into account during audio signal enhancement, this can be configured to provide benefits to the user.

By taking into account both the transducer effect and environment, additional information/data may be collected and stored aside from the threshold values obtained. This data is specific to the transducer used, as well as the environment noise composition at the time of data collection. The transducer characteristics can even be determined by the user indicating to the system the brand/model of the earphone before undergoing the test protocol. The environment noise can be separately sampled and analyzed during the test.

In view of the foregoing, it will be understood that isolating the characteristics of a particular user's audio perception requires accounting for a number of audio device characteristics, as well as either controlling or accounting for environmental noise. These requirements add complexity to the data acquisition and/or processing components needed in a profiling system. A need therefore exists for a more practical and efficient system and method of providing customized enhanced sound for a particular user. Further, different users may have sound enhancement preferences that are determined by other considerations than frequency-specific audio perception, comfort levels, or tinnitus, including personal aesthetic taste, for example. Thus, there is also a need for a sound enhancement system that permits a user to manually adjust the audio output of a device, starting from an automatically produced default enhanced signal.

SUMMARY OF THE INVENTION

According to one aspect of the invention, a system and method are provided for producing a typically normal hearing experience in a hearing impaired individual. Specifically, the invention includes capturing a person's audio hearing characteristics to produce an individualized audiological profile; analyzing the individualized audiological profile; producing a processed result; and then automatically enhancing the output signals from an audio reproduction apparatus to provide the individual with a processed result as a satisfactory audio experience.

In a preferred embodiment, the audiological profile used to produce the process result is obtained using a device part or the whole of which has not been calibrated. By finding the thresholds over a range of frequencies in any environment using any transducer, a set of data is captured representing a subject's "hearing profile" measured for that specific pathway. The data thus captured would generate a shaped "auditory profile" that only applies to the signal pathway that has been measured in the environment in which it was measured. This data set may then be used as a template upon which the signal processing engine could enhance the audio signal. This method would effectively establish a relationship between the electronic signal in a device and a user's auditory perception of the sound generated from the device in the environment in which the shaped profile was captured.

The processed result includes individual hearing parameters of frequency-based loudness enhancement and other hearing-related characteristics to address and complement an individual's hearing needs. It accomplishes this activity as closely as possible to a normal hearing standard while maintaining a margin of safety to protect against excessive loudness that may cause discomfort or further hearing damage. The individual user may self-administer a hearing test using a personal device, such as an MP3 player or a smartphone. The individualized audiological profile typically contains the following: (1) measurements at typically three loudness levels (namely the most comfortable, the uncomfortable, and the minimum audible level) at each audiometric frequency; (2) measurements from a tinnitus test, with tinnitus loudness and pitch; and (3) a user's customization settings. Customization settings may include those settings appropriate for or chosen by the user to be implemented in a noisy environment. This aspect of the invention is useful for any individual seeking an enhanced hearing experience, whether having hearing within normal range or hearing that is impaired. Thus, the system is useful as a hearing aid.

In a specific embodiment, separate functions of the invention may be incorporated into a single multifunction device or multiple devices. A software-based system may be implemented according to the invention on any computerized apparatus, such as a personal computer, a smart phone, personal amplifier or combination thereof with local, removable, or remote storage of an individualized audiological profile. The software-based system performs a variety of functions. It captures frequency-specific personal audio hearing characteristics and analyzes the characteristics to generate an individualized audiological profile. This profile is stored either locally or remotely and later used as a control input to enhance audio from an appropriately programmable audio reproduction apparatus, such as the personal computer, smart phone, personal amplifier or combination thereof, through which an audio program or like source material (prerecorded music or phone conversation, for example) is reproduced.

At the audio reproduction apparatus, the signal processing comprises receiving audio program material in the form of audio signals in the time-domain; capturing and analyzing the current frequency composition of the acoustic environment to produce therefrom a current environment profile reflecting the ambient sound environment that is updated as the acoustic environment changes; applying the stored individualized audiological profile and the current environment profile to the audio program material through a set of filters, such as finite impulse response digital filters, to calculate a set of desired gains at pre-selected frequencies;

modifying the audio program material; converting the modified audio program material from the time domain to the frequency domain; analyzing the loudness tolerance level for the modified audio program material by comparing the levels with the person's sound loudness tolerance level (hereinafter also uncomfortable loudness level—UCL) at each audiological frequency; adjusting the loudness at selected frequencies where the individual's UCL is exceeded to produce a frequency domain audio signal; converting the frequency domain audio signal to its equivalent time domain audio output signal; and conveying the time-domain audio output signal to the individual. The audio hearing characteristics may be stored locally or remotely, and the analysis of the hearing characteristics and processing to produce the individualized audiological profile may be performed and stored locally on a personal device, or it may be stored remotely at a central hearing processing center connected through telecommunication links such as the Internet, and retrieved as needed for reproduction of sound according to the principles of the invention.

In various embodiments of the invention, the principles of the invention may be applied to audio programs in the presence of environmental sources such as white or colored noise, in the presence of a tinnitus condition, or both.

Tinnitus can be mitigated in accordance with the invention. Tinnitus loudness refers to the sensational level (SL) of an individual's tinnitus as calculated by subtracting the minimum audible level of tinnitus pitch from the intensity of the individual's tinnitus. While different approaches may be used to address tinnitus, one approach is through the use of sound therapy. Tinnitus relieving signals are generated according to the tinnitus pitch and loudness that have been measured when capturing the audio hearing characteristics that are used to form the individualized audiological profile. These generated relieving signals are used independently (without other enhancement) or embedded as part of the reproduced sound.

Another aspect of the invention allows any user of a computerized apparatus to readily produce an individualized audiological profile to complement the individual's personal needs while providing a safety margin against discomfort and hearing damage, with the goal of bringing the user's hearing experience back to "normal." In addition, self-administered as well as professionally administered and other audio hearing characteristics test results can be captured, analyzed, and stored locally and/or remotely. While the normal hearing experience is achieved automatically, users may optionally be provided with the capability of modification of the established normal hearing experience according to their liking.

The invention recognizes the significant gap between hearing test results and sound enhancement processes and provides a bridge between the two. The hearing characteristics analyzed according to a proven methodology are the dictating factors of the sound enhancement process resulting in a normal hearing experience.

In addition to the factors which are stored during the process that captures the user's listening characteristics, there are other user factors which will affect the audio signal enhancement. These are user preferences, which include the level of enhancement applied by the system (e.g. 25%, 50%, 75% or 100%), as well as the preferred adjustment according to the type of audio (e.g. music or speech) being processed.

For the level of enhancement, it is the intended adjustment by the user which affects the parameters used for audio processing. This adjustment deals with the user's comfort, adaptation in using the technology, and choice of enhancement level. The user may select different levels of enhancement (e.g. 25%, 50%, 75% or 100%).

Another "user preference" can be the choice of headset or ear phone and the physical fitting of the headset over the ear or of the ear phone into the bowl of the ear or ear canal. For any particular audio device, this can vary from time to time but tends to be a relatively consistent habit or way of fitting for an individual. However, due to the different build of different models, these will, due to their physical nature (e.g., size and shape) fit differently over or into the ear. These factors also contribute to the differences in shaped "auditory profiles" that may be obtained for an individual according to the various models of earphones and their physical fit in relation to that individual user's ear.

For preferred adjustment according to type of audio, the system can be configured to enhance the audio according to the type of audio signal, making parameters used for audio enhancement more suitable for the characteristics of music, even the genre of the music, or speech.

All of the factors, including the individual's thresholds (which is the shaped "auditory profile"), transducer characteristics, noise composition during testing and user preferences are stored in the system. The shaped "auditory profile" can be viewed as representing the relationship along the signal pathway from the audio signal to the user's perception of the sound, which is specific to the signal pathway that has been measured; the "auditory profile" can be used to produce parameters for audio signal enhancement according to a set of rules.

The invention will be more clearly understood by reference to the following detailed description in connection with the accompanying drawings.

BRIEF DESCRIPTION OF THE DRAWINGS:

FIG. 17 is a flow chart illustrating a parameter creation process according to an aspect of the invention.

FIG. 18 is a flow chart illustrating an individualized audio output generation process according to an aspect of the invention.

FIG. 24 is a flow chart illustrating a profile selection process according to an aspect of the invention.

FIG. 25 is a flow chart illustrating a profile creation process according to an aspect of the invention.

DETAILED DESCRIPTION OF SPECIFIC EMBODIMENTS

Figure 1A:
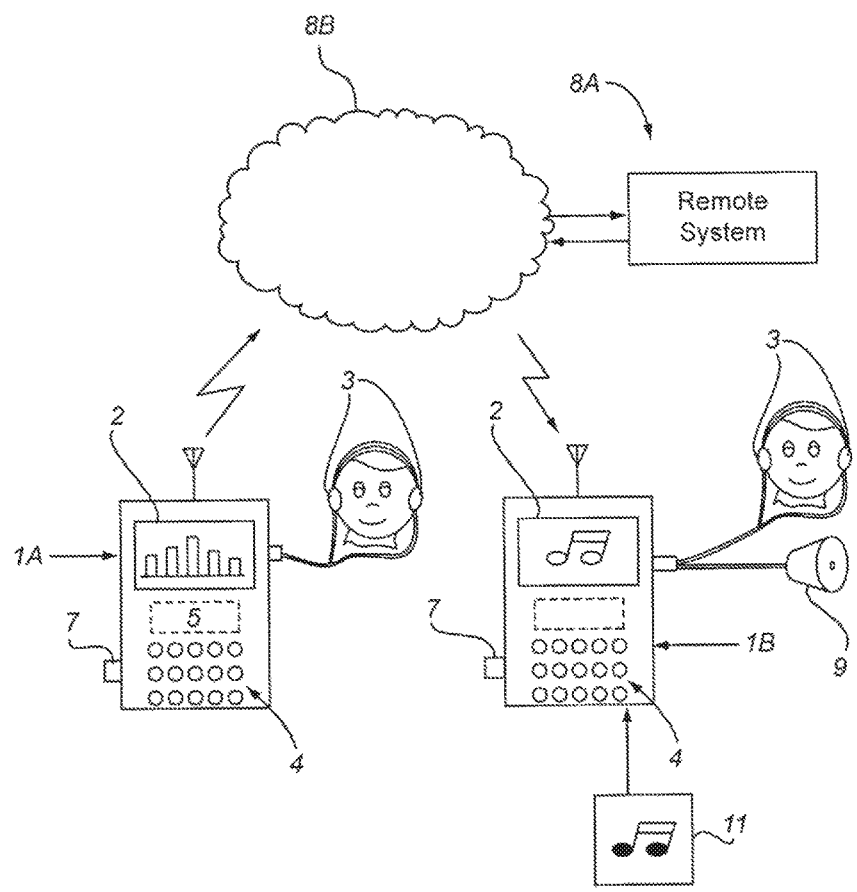
FIG. 1A is a high-level block diagram illustrating uses of one or more personal devices in connection with a remote storage medium in accordance with an aspect of the invention.

Referring to FIG. 1A, a high-level block diagram of a personal device 1 is shown with representative environmental elements. The device 1A has a display 2, a set of earphones 3 and a control interface 4, such as a keyboard. The device 1A stores or receives a test regimen 5 that is activated by its individual user via the control interface 4, which then interacts with the hearing of the user who responds as hereinafter explained. An individualized audiological profile as hereinafter explained is generated which is stored locally in the device 1A, or on a removable storage device (thumb drive or nonvolatile memory card) 7, or remotely in a remote analysis and storage system 8A accessible via telecommunication links 8B. The individualized audiological profile is used on the same or similar device 1B to modify its audio signal output to the same earphones 3 or to a loudspeaker 9. The audio signal output is based on input of programming material 11 whose frequency-dependent and time-dependent characteristics are regulated by the individualized audiological profile and an environment profile developed from the current environment as hereinafter explained.

Figure 1B:
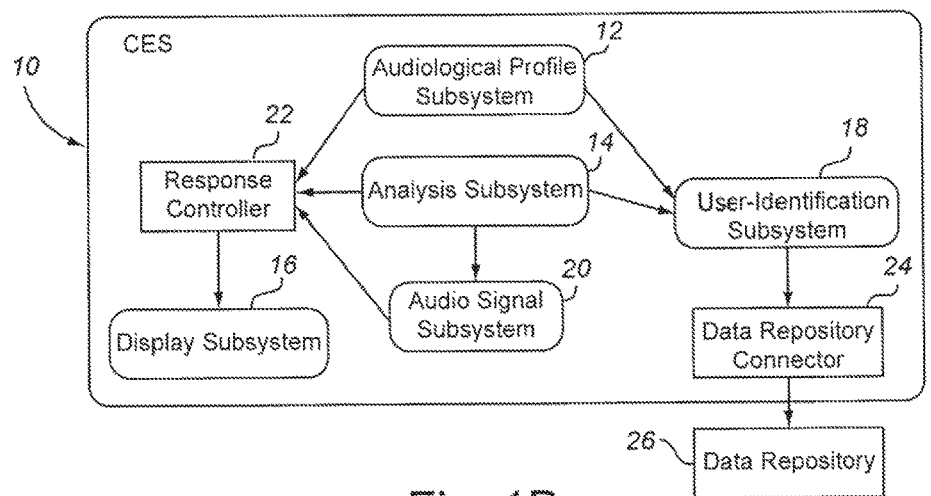
FIG. 1B is a high-level block diagram of a system according to an aspect of the invention.

Referring to FIG. 1B, according to an aspect of the invention, a Customized Enhanced Sound™ (CES) system 10 is provided having subsystems and classes for information input, audiological profiling, analysis, display, user identification, response control, and data repository. A class as used herein is a description of a software-based group of objects with similar properties, common behaviors, common relationships, and common semantics. A subsystem is a set of classes collaborating to fulfill behavior(s) for which the subsystem is responsible. Each class plays a role in the subsystem by handling different responsibilities and communicating with each other to fulfill each responsibility.

Implemented in software on a general purpose hardware platform of appropriate capabilities, the system 10 of device or devices 1A/1B/8A provides the dual functions of testing to develop profiles and of sound reproduction in a particular environment. In the testing mode, the system 10 interactively measures personal hearing capabilities in one function (typically prior to use for subsequent storage) and measures environmental sound/noise in another function (typically contemporaneous with reproduction). The system 10 stores the individualized audiological profile locally or remotely. The system 10 stores the environment profile locally. Analysis of raw data to generate the individualized audiological profile may also be performed either locally or remotely (via telecommunication links). In the reproduction or playback mode, the system 10 modifies a source audio program (input audio signals) according to the individual and environment profiles to adapt the program to the hearing capabilities and preferences of the individual user. In a specific embodiment, the system 10 captures and measures, or receives captured data, analyzes the data, generates target gain for each audiometric frequency, applies the target gain and/or tinnitus relieving signals to the audio signal, and forms the enhanced audio output signals with safeguards against uncomfortable or damaging loudness.

Components of the CES system 10 include an audiological profile subsystem 12, analysis subsystem 14, display subsystem 16, user-identification subsystem 18, audio signal subsystem 20, response controller 22, and data repository connector 24 in communication with a data repository 26 (which can be local or remote).

Audiological Profile Subsystem

The audiological profile subsystem 12 conducts tests performed separately on each ear, as related to the user's audio hearing characteristics. The subsystem responsibilities include: determining a user's hearing characteristics; determining a user's tinnitus characteristics; determining a user's most comfortable loudness level for each audiometric frequency; determining a user's uncomfortable loudness level for each audiometric frequency; generating audio test signals on demand; determining the user's audio hearing characteristics from a professionally administered hearing test; and generating the individualized audiological profile.

Figure 2:
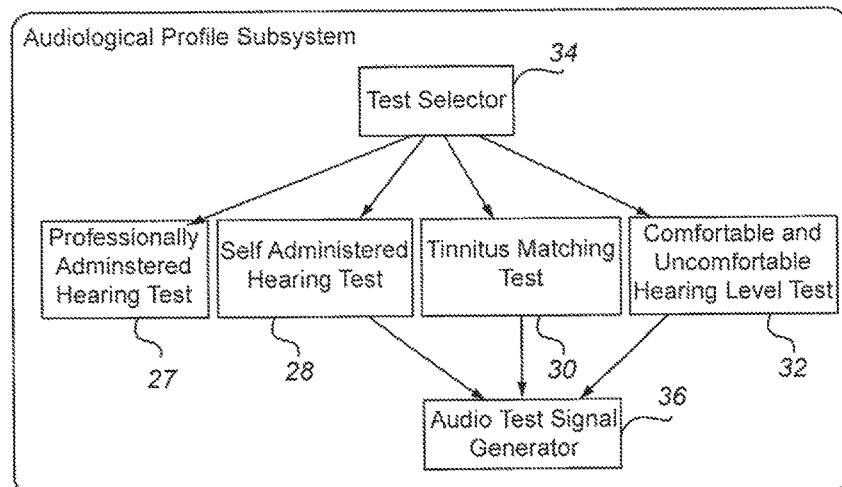
FIG. 2 is a high-level block diagram of an audiological profile subsystem according to an aspect of the invention.

Referring to FIG. 2, the classes in the audiological profile subsystem include: a professionally administered hearing test class 27; a self-administered hearing test class 28; a tinnitus matching test class 30; a Comfortable and Uncomfortable hearing level test class 32; a test selector 34; and an audio test signal generator class 36.

Analysis Subsystem

The analysis subsystem 14 analyzes the user's individualized audiological profile and produces a processed result which is used by the audio signal subsystem for the generation of the enhanced audio output signals. The subsystem responsibilities include interpreting the user's audiological profile; determining needed audio gains; determining the type or types of relieving sounds to generate; generating the specified relieving sound; and handling the user's customization settings. The types of relieving sounds supported are: a) music, b) narrow-band noise, c) broadband noise, d) environmental sound, and e) pure tone audio signals.

Figure 3:
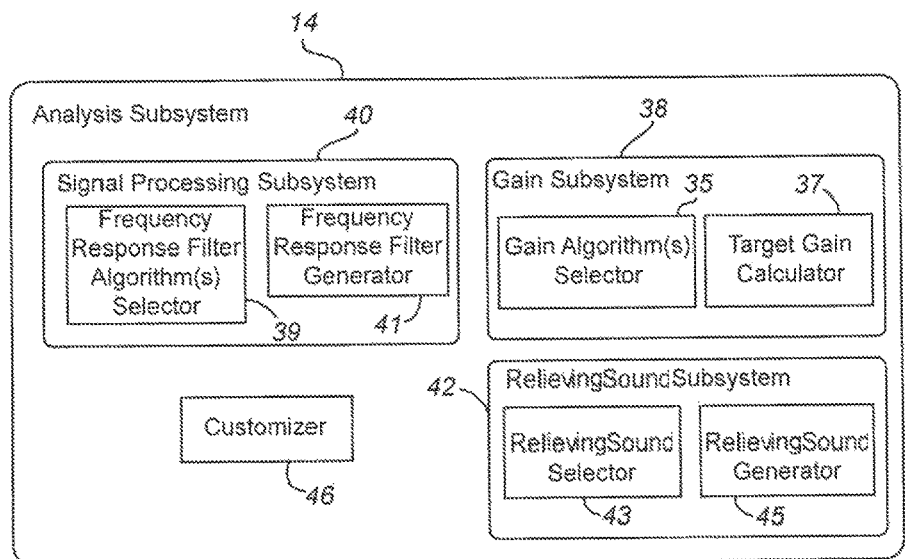
FIG. 3 is a block diagram of an analysis subsystem according to an aspect of the invention.

Referring to FIG. 3, the subsystems and classes of the analysis subsystem 14 include: gain subsystem 38, signal processing subsystem 40, relieving sound subsystem 42, and customizer class 46. Within the gain subsystem 38 the classes are a gain algorithm selector 35 and a target gain calculator 37. Within the signal processing subsystem 40 the classes are an algorithm selector 39 and a filter generator 41. Within the relieving sound subsystem 42 the classes are a relieving sound selector 43 and a relieving sound generator 45.

User-Identification Subsystem

Figure 4:
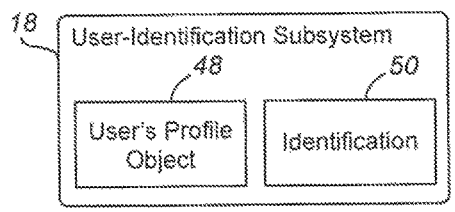
FIG. 4 is a block diagram of a user-identification subsystem according to an aspect of the invention.

The user-identification subsystem 18 manages the user identification process and maintains individualized audiological profiles. The subsystem 18 responsibilities include determining the identity of the user; verifying the identity of the user; and maintaining the user's individualized audiological profile. Referring to FIG. 4, the classes in the user-identification subsystem 18 include the profile object 48 and identification of the user 50.

Audio Signal Subsystem

Figure 5:
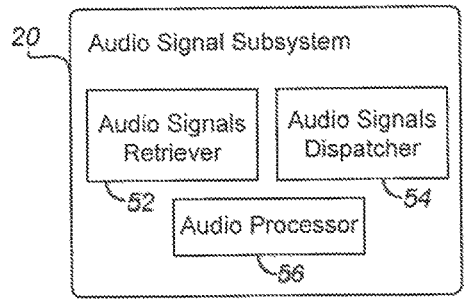
FIG. 5 is a block diagram of an audio signal subsystem according to an aspect of the invention.

The audio signal subsystem 20 manages all issues related to the storage and utilization of audio signals. The subsystem responsibilities include: retrieving pre-enhanced audio signals from an audio programming source; generating from the pre-enhanced audio signals the enhanced audio signals based upon the processed result from the analysis subsystem; and dispatching the enhanced audio signals. Referring to FIG. 5, the classes in the audio signal subsystem 20 include an audio signals retriever 52, audio signals dispatcher 54, and audio processor 56.

Display Subsystem

The display subsystem 16 provides all the user interface elements that the user interacts with when using the invention and may be of conventional design appropriate to the system 10.

Data Repository Connector

The data repository connector 24 is a class that manages the connection with the data repository 26. The class responsibilities include: establishing a database connection; generating a database query statement(s); retrieving/updating/inserting/deleting data into and from the data repository 26; and retrieving data from the data repository 26.

Response Controller

The response controller 22 is a module that interprets what needs to be displayed based upon on the requests. Its responsibilities include determining and sending the necessary information to be displayed to the display subsystem.

Logical Flow of Framework

Figure 6A:
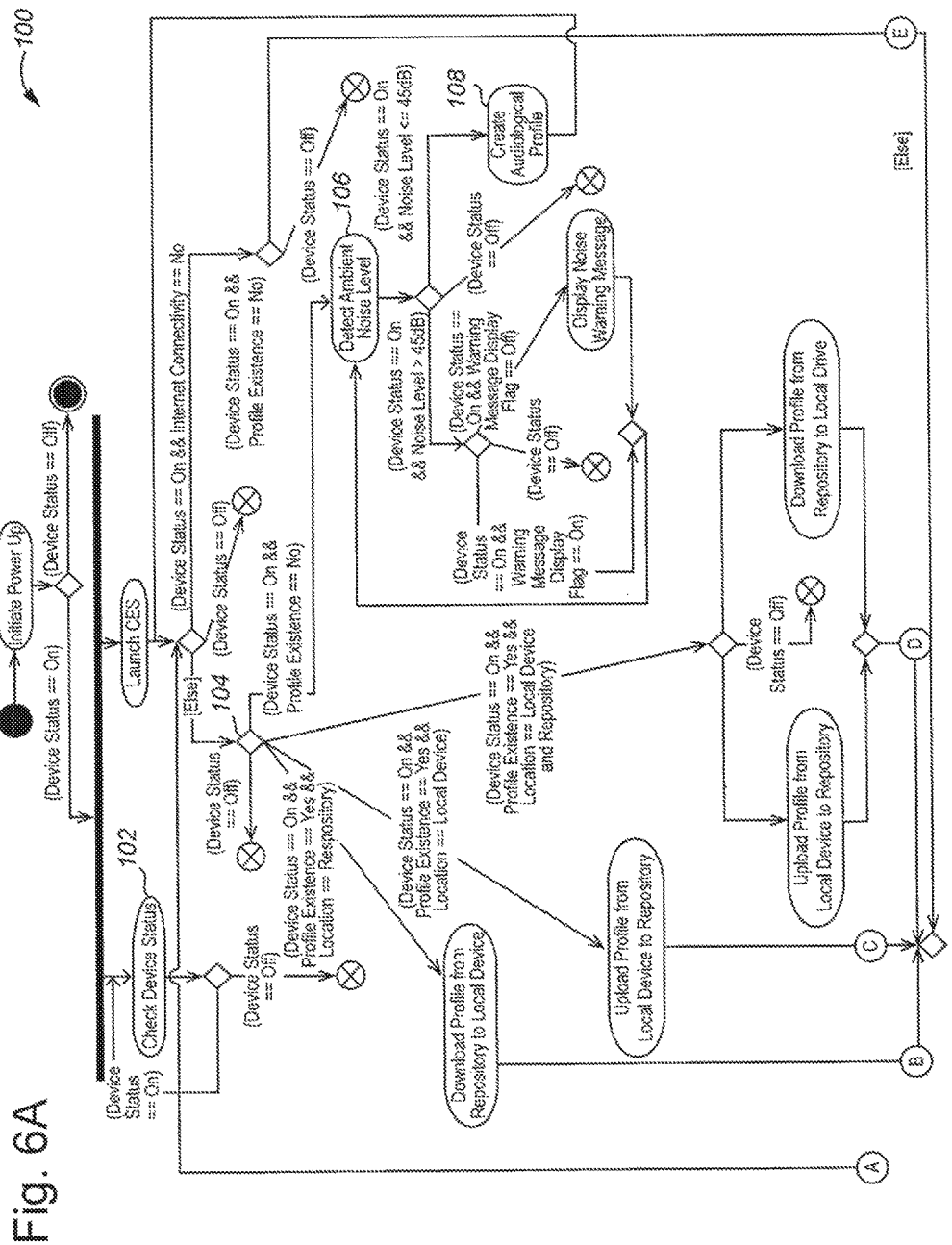
FIGS. 6A and 6B are together an activity diagram of a sound enhancement process according to an aspect of the invention.
Figure 6B:
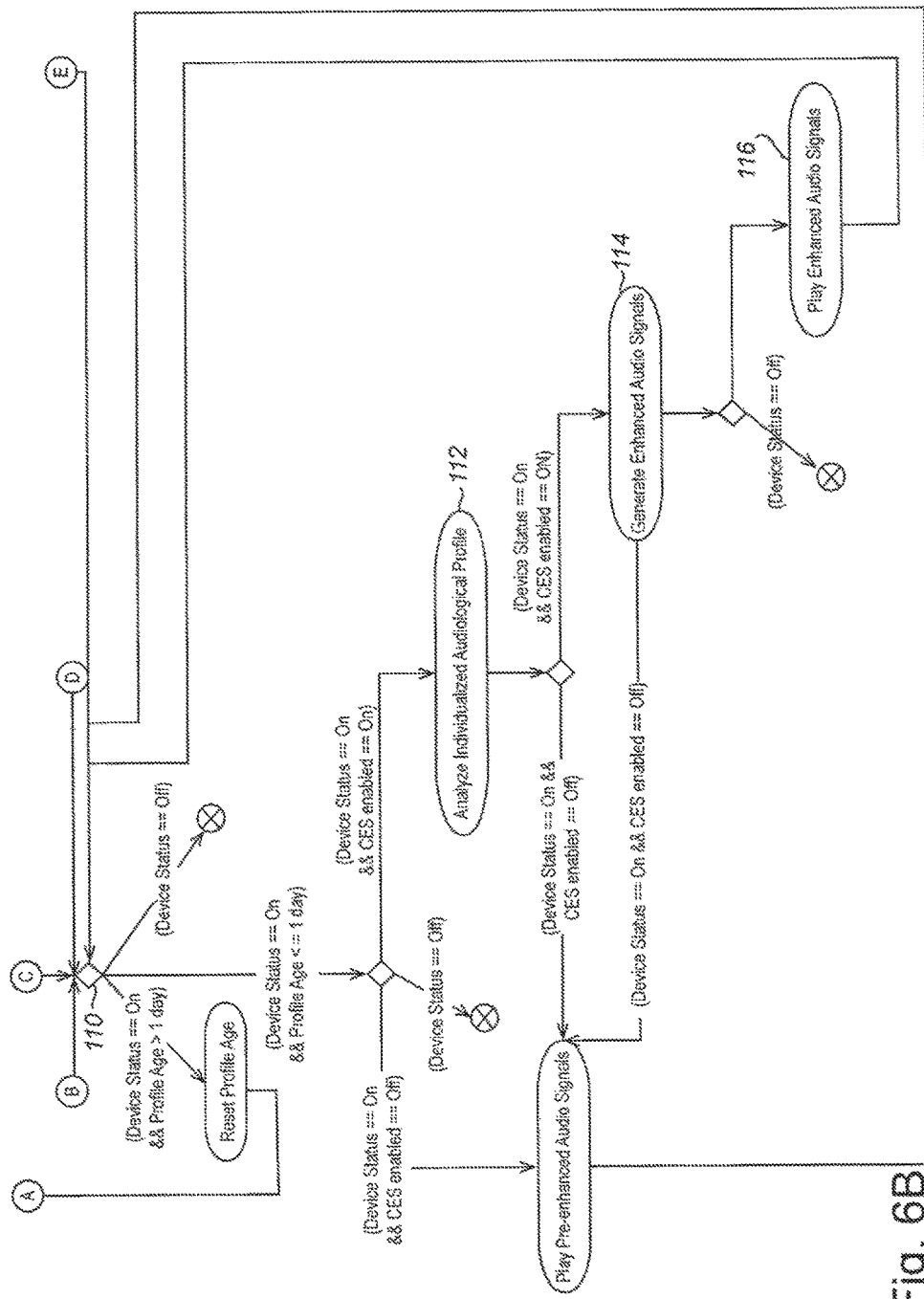
Figure 7:
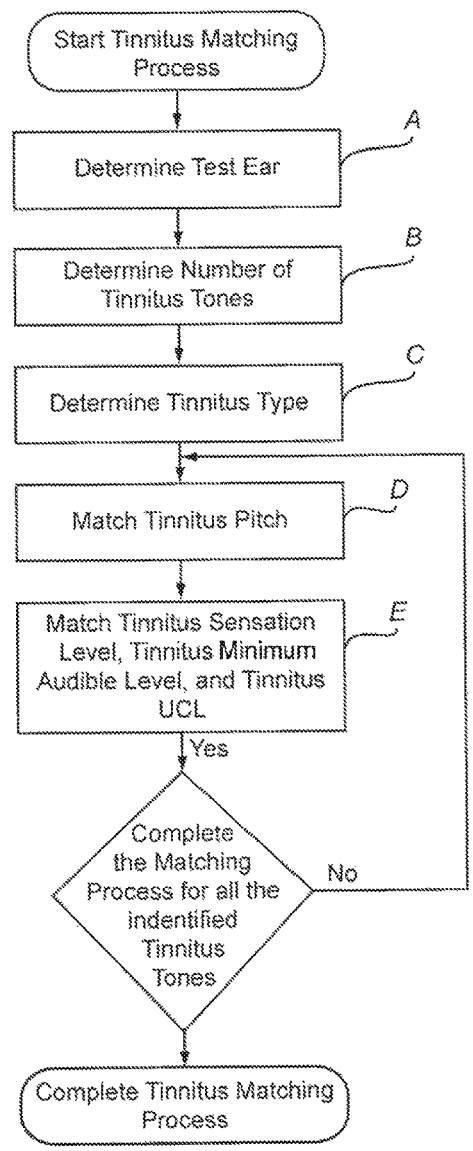
FIG. 7 is a flow chart of a tinnitus matching process according to an aspect of the invention.

FIGS. 6A and 6B and the following paragraphs describe the logical flow of the CES system 10 and process 100 according to an aspect of the invention in an activity diagram. The activity diagram of the software-based system shown in FIGS. 6A and 6B is largely self-explanatory and includes the nodes, basic functionality and interrelationships of elements in the sound enhancement process. The sound enhancement process includes: monitoring user device status 102; determining whether a user profile exists and location in which the profile is stored 104; detecting the ambient noise level 106; generating an individualized audiological profile 108; determining the date and time of the user profile 110; analyzing individualized audiological profile 112; generating the enhanced audio signals 114; and playing enhanced audio of the enhanced audio signals on a user device 116. For several of the major steps of the sound enhancement process, there are several example embodiments provided in outline (pseudo-code) form as follows:

```
Monitor User Device Status (Check Device Status)
    Check for the existence of device's power signal
        If there exists power signal,
            Mark the device status to ON.
        If there exists no power signal,
            Mark the device status to OFF.
    The software-based system performs device status monitoring
constantly and in parallel with the other processes within the sound
enhancement process.
At any given point in time, if the device status equals to OFF,
the software-based system will stop functioning.
        Check for Profile Existence and Location in which the Profile
is Stored
        Check for Internet connectivity
        If there exists no Internet connectivity and the device status equals to
ON
        Check for profile existence
        If the local device has a profile,
            Check for profile age
        If the local device has no profile and the device status equals to ON,
            Detect ambient noise level and generate audiological profile
        If there exists Internet connectivity and the device status equals to
ON,
        Check for profile existence and location of the profile
        If the data repository has the profile and the device status equals to
ON,
            Download the profile from the data repository to local device
            Check for profile age and signal enhancement
        If the local device has the profile and the device status equals to ON,
            Upload profile from local device to data repository
            Check for profile age and signal enhancement
        If both the data repository and the local device have the profile and
``` the device status equals to ON,
 Compare the time stamp of the two profiles
 If the local profile is the most recent and device status equals to ON,
  Upload profile from local device to data repository
  Check for profile age and signal enhancement
 If the profile in the data repository is the most recent and the device status equals to ON,
  Download profile from data repository to local device
  Check for profile age and signal enhancement
 If no profile is found and the device status equals to ON,
  Detect ambient noise level, then generate audiological profile
  Check for Profile Age and Signal Enhancement
 If the profile age is greater than one day old and the device status equals to ON,
  Reset the profile age
  Check for profile existence and location in which the profile is stored
 If the profile age is less than or equal to one day old and the device status equals to ON,
  Check for CES status
  If CES has been enabled,
   Analyze individualized audiological profile
   Generate enhanced audio signals
   Play enhanced audio
  If CES has been disabled,
   Play pre-enhanced audio
   Detect ambient noise level (Environment)
   Measure the level of the ambient noise
 If the ambient noise level is greater than 45 dB and the device status equals to ON
  Display warning message
  Detect ambient noise level
 If the ambient noise level is less than or equal to 45 dB and the device status equals to ON
  Create individualized audiological profile.
The environment profile is updated continually in real time during playback of audio program material. A typical cycle for updating the environment profile is 100 ms. However, updating can occur more or less frequently from a digitized sound sample rate of about 16 ms to 50 ms to several minutes in slow-changing ambient noise environments.
  Generate Individualized Audiological Profile
  Select the type of hearing test to perform
  If the user selects a self-administered hearing test
   Perform pure tone audiometry for each ear separately
   Play an audio signal at each audiometric frequency
   Ask the user to select the minimum audible level at each audiometric frequency
   Repeat the pure tone audiometry until the minimum audible level for all audiometric frequencies have been captured
   Perform uncomfortable hearing test for each ear separately
   Play an audio signal at each audiometric frequency
   Ask the user to select the uncomfortable loudness level at each audiometric frequency
   Repeat the uncomfortable hearing test until the uncomfortable loudness level for all audiometric frequencies have been captured
   Perform the most comfortable hearing test for each ear separately
   Play an audio signal at each audiometric frequency
   Ask the user to select the most comfortable loudness level at each audiometric frequency
   Repeat the most comfortable hearing test until the most comfortable loudness level for all audiometric frequencies have been captured
   Invite user to perform tinnitus matching test
   If the user wants to perform tinnitus matching test
    Perform tinnitus matching test
    Determine the test ear
    Determine tinnitus type
    Match the tinnitus pitch
    Match the tinnitus loudness
   If the user does not want to perform tinnitus matching test
    Skip the tinnitus matching test
  If the user selects professionally administered hearing test
   Enter the air conduction unmasked minimum audible level for all audiometric frequencies for each ear
   Enter the air conduction masked minimum audible level for all audiometric frequencies for each ear
   Enter the bone conduction unmasked minimum audible level for all audiometric frequencies for each ear
   Enter the bone conduction masked minimum audible level for all audiometric frequencies for each ear
   Enter the bone conduction forehead unmasked minimum audible level for all audiometric frequencies
   Enter the bone conduction forehead masked minimum audible level for all audiometric frequencies for each ear
   Enter the uncomfortable loudness level for all audiometric frequencies for each ear
   Enter the most comfortable loudness level for all audiometric frequencies for each ear
    Enter tinnitus matching result
    Enter the result from the speech reception threshold test
    Enter the result from the speech discrimination test
    Enter the audio source used in the speech reception threshold test
    Enter the audio source used in the speech discrimination test
    Create the individualized audiological profile from the captured data As noted above, one regimen of tests is for hearing sensitivity at various frequencies, and another regimen of tests is for individual tinnitus. The tinnitus pitch, tinnitus sensation level, tinnitus minimum audible level and tinnitus UCL test regimen is a process termed the tinnitus matching process. The type of tinnitus considered by this invention is: subjective, namely the perception of sounds without any external sound sources. The regimen is carried out in five steps. Referring to FIG. 7, the steps are: test ear determination (A); tinnitus tone number determination (B); tinnitus type determination (C); tinnitus pitch determination (D); and tinnitus sensation level determination (E). These steps are explained below in greater detail.

Step 1: Test Ear Determination

Figure 8:
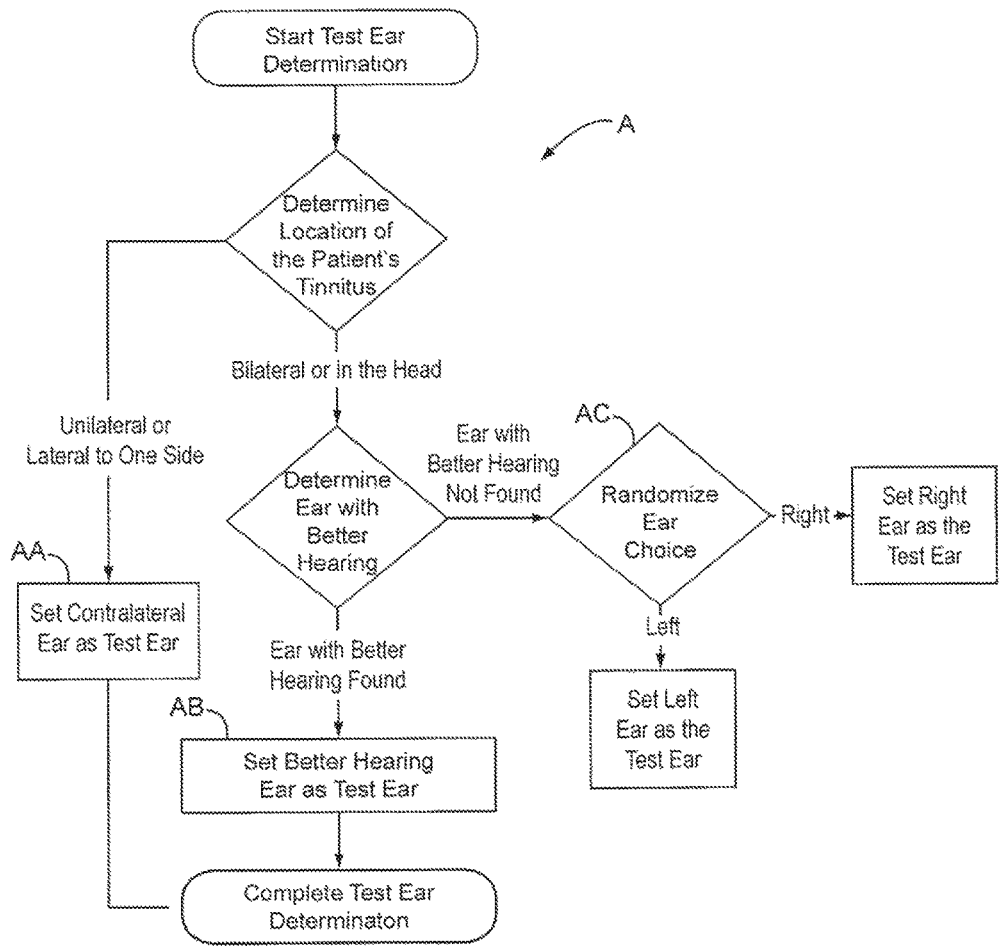
FIG. 8 is a flow chart of the test ear selection process of the tinnitus matching process according to an aspect of the invention.

The purpose of this step is to determine which ear to use as the test ear. A user can perceive tinnitus at various locations: unilateral, bilateral, and head. Depending on the reported location of the tinnitus, the test ear would be selected accordingly. FIG. 8 outlines the procedure involved and is largely self-explanatory. The following points relate to specific steps.

If the reported location of the perceived tinnitus is unilateral, the contralateral ear would be considered as the test ear (AA). The choice of using the contralateral ear is to minimize the possible interference between tinnitus and test stimuli and to increase the accuracy of the test result.

If the reported location of the perceived tinnitus is lateral to one side, the contralateral ear would be considered as the test ear (AA). The choice of using the contralateral ear is to minimize the possible interference between tinnitus and test stimuli and to increase the accuracy of the test result.

If the reported location of the perceived tinnitus is neither unilateral nor lateral to one side of the individual's head, the ear with better hearing would be considered as the test ear (AB). In the case where there is no difference in the hearing ability between two ears, the test ear would be chosen randomly (AC).

Step 2: Number of Tinnitus Tones Determination

Figure 9:
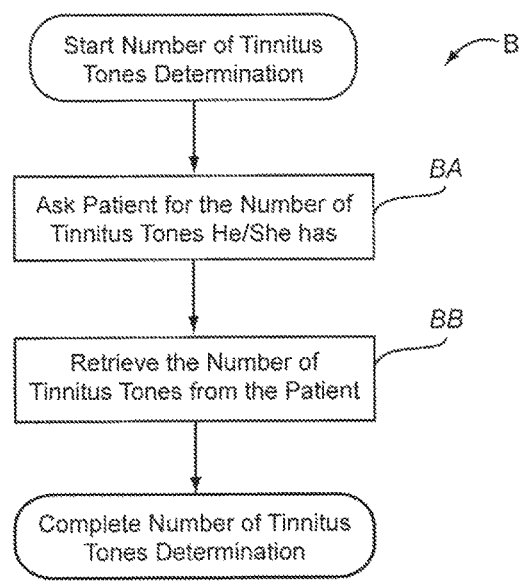
FIG. 9 is a flow chart of the tone number determination test of the tinnitus matching process according to an aspect of the invention.

Tinnitus is perceived as tonal. The purpose of this step is to determine the number of tinnitus tones the user perceives. Referring to FIG. 9, the determination process would request the user for the number of tinnitus tones the user has and saves the inputted value (BA). In one embodiment of this invention, the test focuses on the most troublesome tinnitus tone (often a personal, subjective determination by the individual). In another embodiment, the test focuses on the two most significant tinnitus tones. Yet, in another embodiment, the test and its profiling supports any number of tinnitus tones in which case all such tones would be noted (BB).

Step 3: Tinnitus Type Determination

Figure 10:
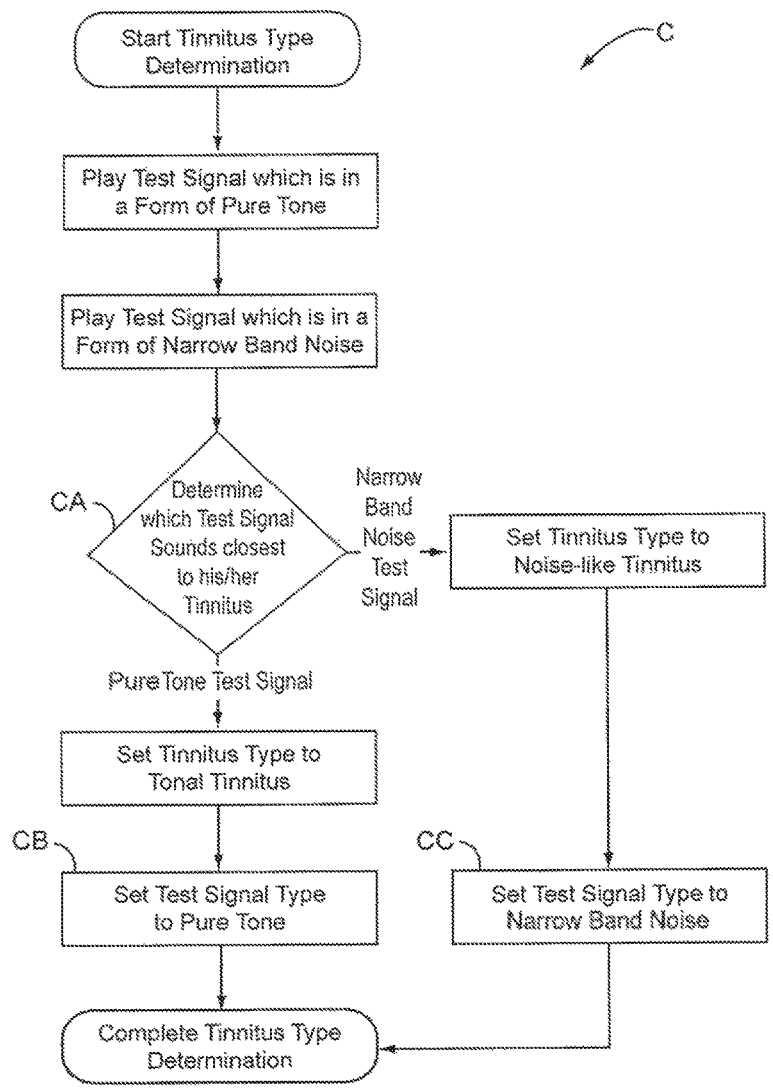
FIG. 10 is a flow chart of the tinnitus type determination process of the tinnitus matching process according to an aspect of the invention.

The purpose of this step is to determine the type of tinnitus (tonal tinnitus or noise-like tinnitus). FIG. 10 illustrates this step. The procedure sets the test signal type accordingly (CA). If the user has tonal tinnitus, the test signal type will be in a form of pure tone (CB). If the user has noise-like tinnitus, the test signal type will be in a form of narrow-band noise (CC).

In one embodiment of this invention, the determination process begins by playing two test signals at 4000 Hz to a user, one in a form of pure tone and the other in a form of narrow band noise. The choice of playing the test signals at 4000 Hz is because most people report having tinnitus in the range of 4000 Hz. The user is requested to compare the test signals and select the one which sounds closest to their tinnitus. From the user's choice in test signal, the type of tinnitus will be derived and the test signal type is set accordingly.

Step 4: Tinnitus Pitch Determination

The purpose of this step is to measure the user's perceived tinnitus pitch. The determination process would play test signals for a range of audiometric frequencies. Each test signal is played at 10 dB SL, meaning 10 dB above the pre-measured minimum response level for the corresponding frequency. The user would select the one that sounds closest to the user's own tinnitus pitch.

In one embodiment of this invention, the user is required to repeat the Tinnitus Pitch Determination three times and the final matched tinnitus pitch would be the average of those measurements. If the user has more than one tinnitus tone, the user would have to perform the Tinnitus Pitch Determination six times, three for each tinnitus tone.

Various methods may be used for measuring tinnitus pitch. In one embodiment of this invention, the discrete-frequencies method is used. The set of test signals will be in a form of discrete data. The determination process, using a two alternative forced-choice approach, presents pairs of test signals and the user would choose the one that is closest in pitch to the user's tinnitus.

Figure 11:
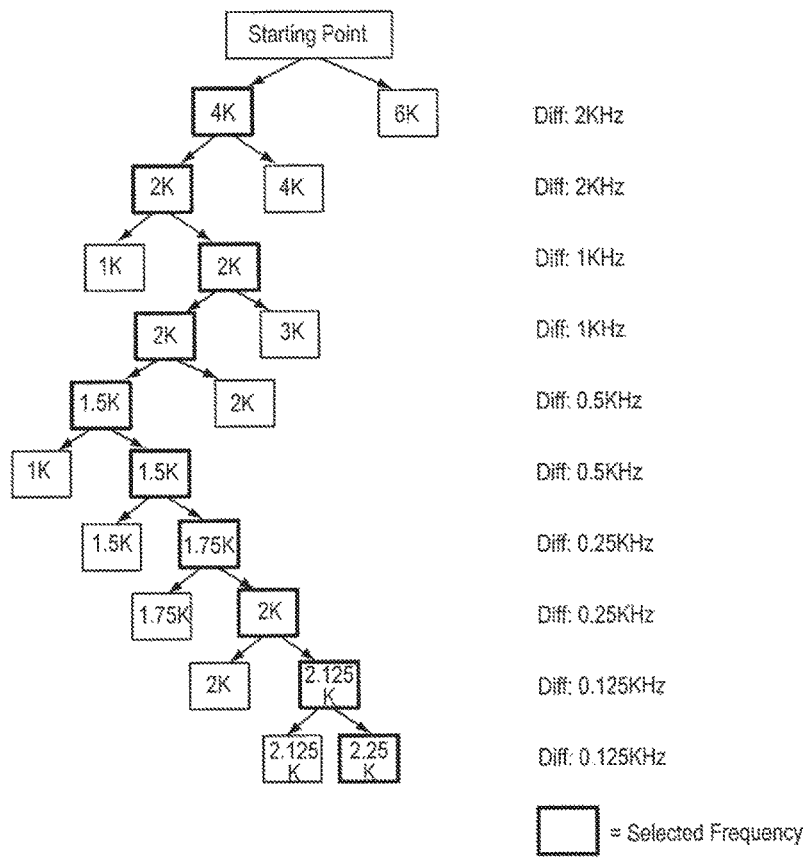
FIG. 11 is a diagram of the test signal tone to tinnitus tone selection process of the tinnitus matching process according to an aspect of the invention.
Figure 12:
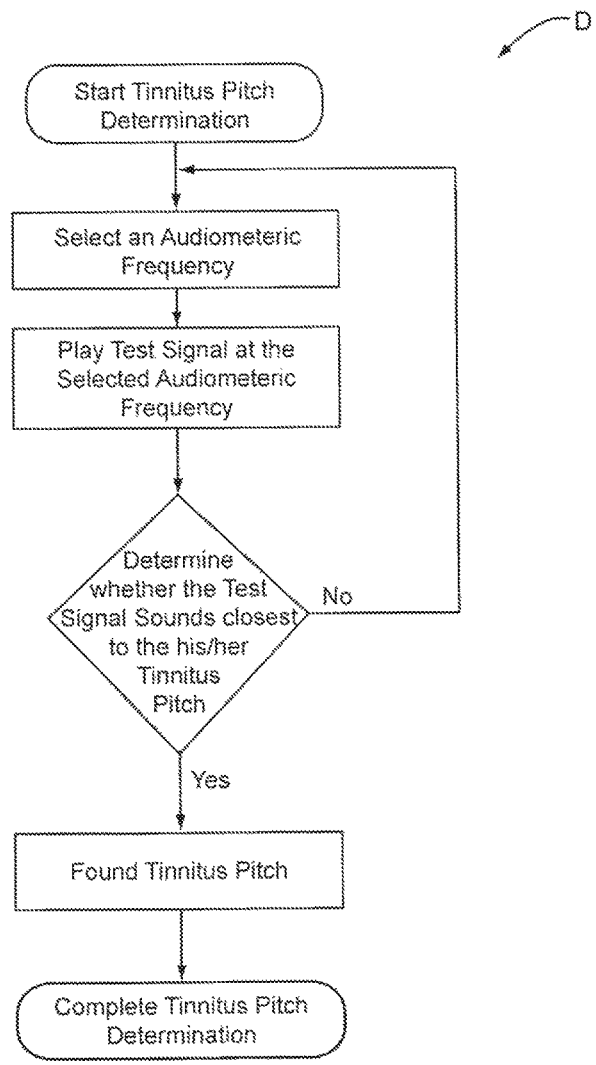
FIG. 12 is a flow chart of the tinnitus pitch determination process of the tinnitus matching process according to an aspect of the invention.

FIG. 11 is one example of the tinnitus determination process. The determination process begins at 4000 Hz. This is chosen because most users report to have their tinnitus at approximately 4000 Hz. The test completion criterion is to obtain an accuracy of 125 Hz for all frequencies. In another embodiment of this invention, the continuous-frequencies method is used. Referring to FIG. 12, the set of test signals may take on values within a finite interval of frequencies. The user picks the one that is close in pitch to the user's tinnitus.

Figure 13A:
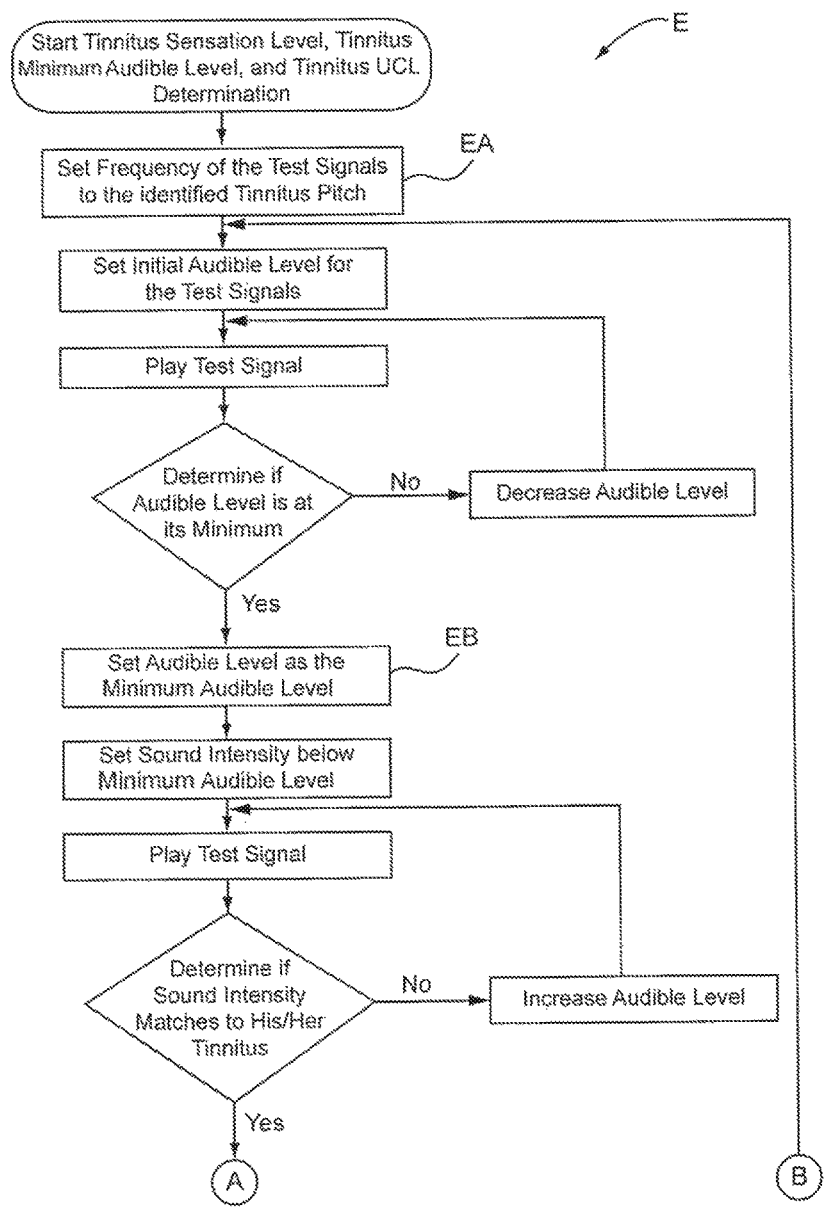
FIGS. 13A and 13B are together a flow chart of the three-level tinnitus test for each tinnitus pitch of the tinnitus matching process according to an aspect of the invention.
Figure 13B:
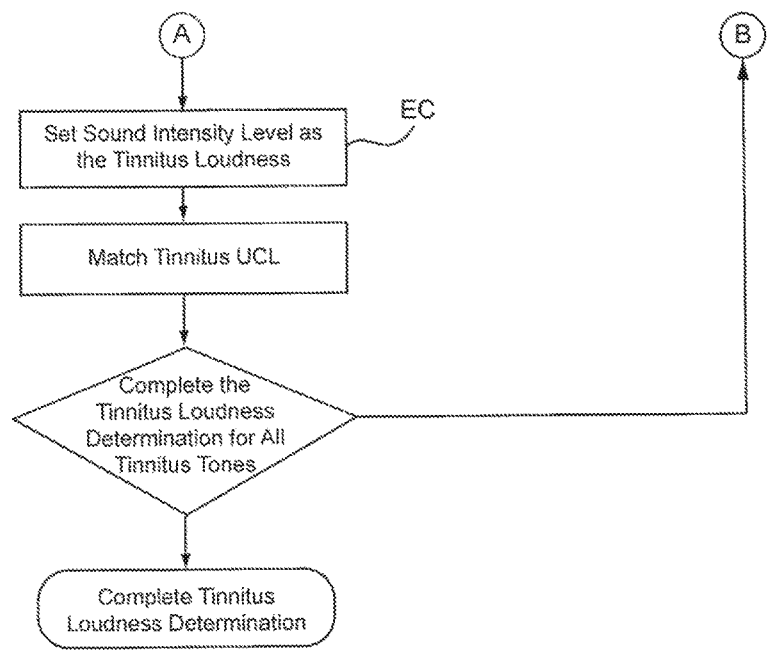

Step 5: Tinnitus Sensation Level, Tinnitus Minimum Audible Level, and Tinnitus Uncomfortable Loudness Level Determination The tests of the three levels of minimum sensation, comfortable and UCL are applied to each tinnitus tone. To the extent that the general three-level test may require illustration; the flow chart of FIGS. 13A and 13B is exemplary. In the multiple-characteristic test illustrated in FIGS. 13A and 13B, the determination begins by setting the frequency of test signals to the identified tinnitus pitch (EA). The next task is to identify the minimum audible level at the tinnitus pitch (EB). The determination process plays test signals at various audible levels and the user is asked to identify the one which the user considers as the minimum audible level. This is an iterative process. Then, the test is to identify the sensation level of their tinnitus. During the determination process test signals are played at various audible levels starting at the level below the minimum audible level. The user is asked to identify the test signal which is equal in loudness to the user's tinnitus. At this point the sound intensity is set as the Tinnitus Loudness (EC). The Tinnitus Sensation Level is calculated by subtracting the Tinnitus Minimum Audible Level (EB) from the Tinnitus Loudness (EC).

In one embodiment, the tinnitus uncomfortable loudness level (TUCL) is captured by playing a narrow band noise of an identified tinnitus pitch to the user and requests the user to identify the level at which the loudness of the noise causes discomfort. In another embodiment, the user is required to repeat the Tinnitus Sensation Level and Tinnitus Minimum Audible Level Determination three times. The final matched sensation level will be the average of those measurements. If the user has more than one tinnitus tone, they may be required to undergo the determination process.

The individualized audiological profile, including the results of analysis of the tinnitus tests, is obtained prior to sound reproduction, i.e., the sound enhancement process. This profile may be updated on any scheduled basis, but it is typically updated on a daily basis to ensure the sound enhancement process is current.

Figure 14:
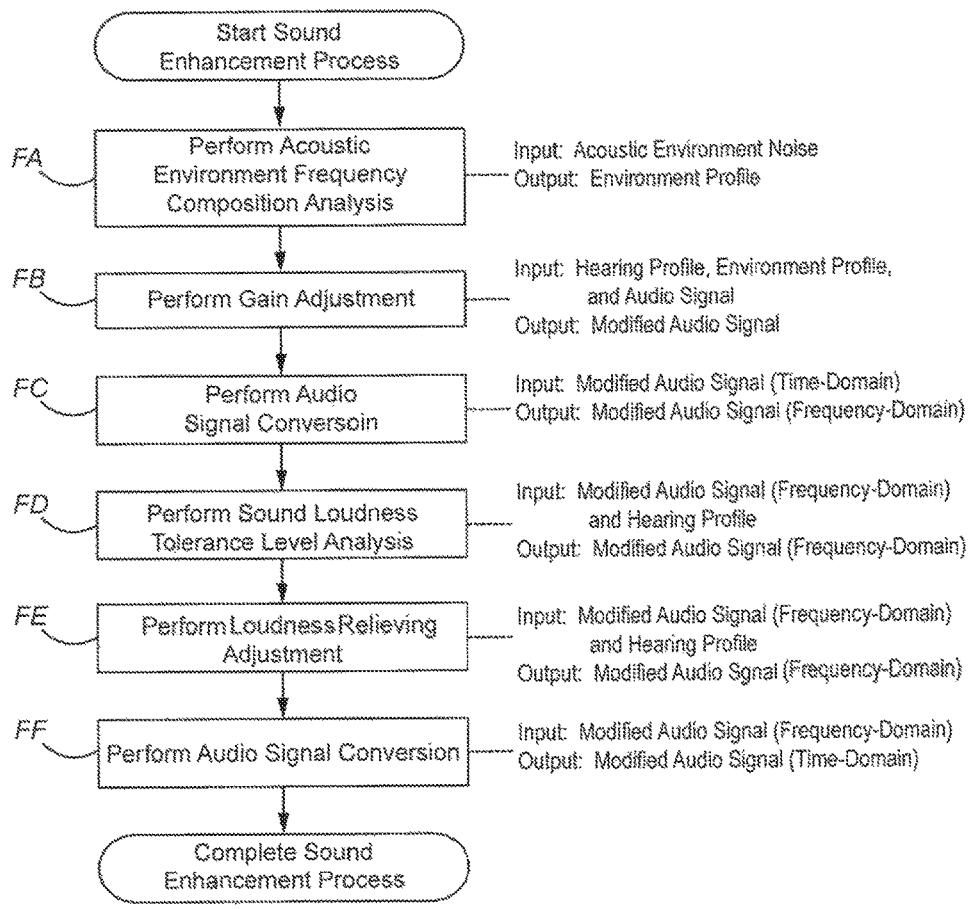
FIG. 14 is a flow chart of the sound enhancement process according to an aspect of the invention.
Figure 15:
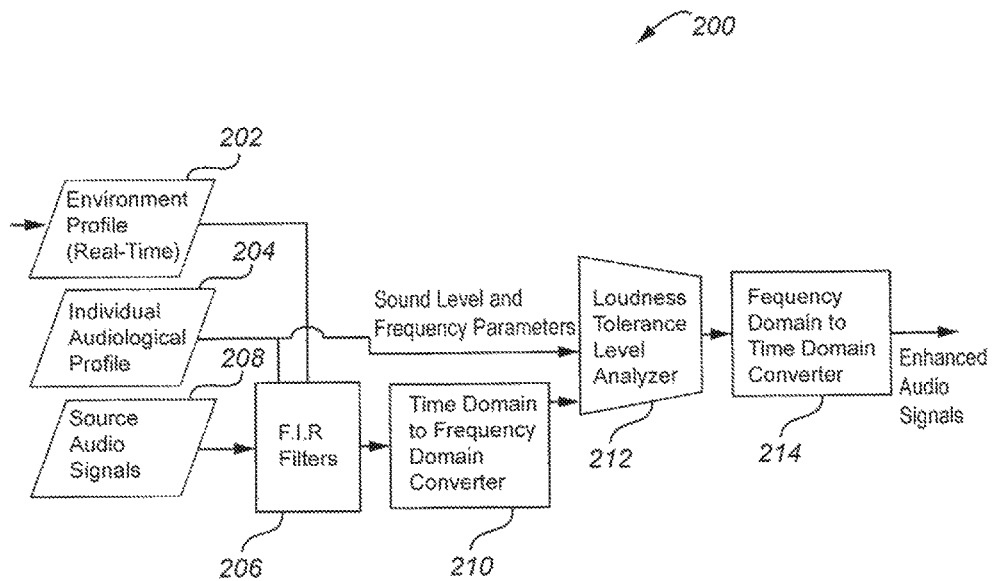
FIG. 15 is a high-level block diagram of a device having the capabilities of the process of FIG. 14.
Figure 16:
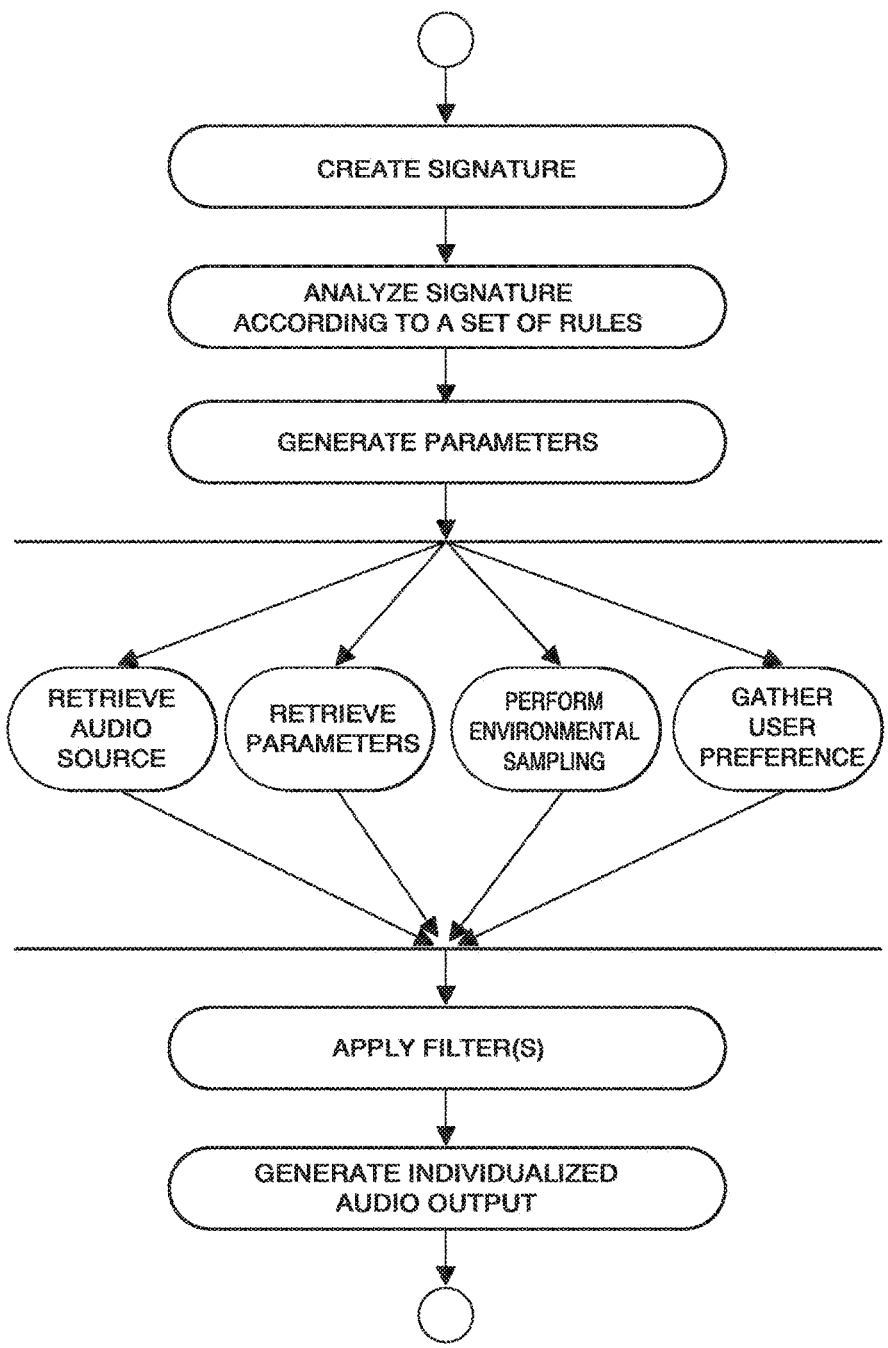
FIG. 16 is a flow chart illustrating a progression from the creation of an auditory profile to the generation of enhanced audio output to an individual according to an aspect of the invention.

A sound enhancement process according to the invention is broadly summarized in FIG. 14. It depicts the processing of audio program material as an audio signal in conjunction with the individualized audiological profile 204 and preferably the latest, i.e., current, environment profile 202 as further depicted in FIG. 15. The sound enhancement process begins with an acoustic environment frequency composition analysis (FA). The system automatically captures and analyzes the frequency composition of the acoustic environment. As described above, it then generates the environment profile 202. The system provides the stored individualized audiological profile 204 comprising the minimum audible levels, sound loudness tolerance levels, and current environment profile, along with an audio signal to be adjusted for gain (FB). The environment profile and the individualized audiological profile are used to derive the coefficients or parameters for a filter(s), such as finite impulse response (FIR) filter(s) 206. The filter(s) are used to provide desired frequency-specific gains which are determined based upon the individualized audiological profile and audio signals 208 of the audio program material from any source. They are applied through the filter(s) which modify the passed-in audio signal accordingly. With a modified audio signal generated, the system converts it from a time-domain representation to a frequency-domain audio signal through a Fourier analyzer 210 (FC). Thereafter, the frequency domain representation is applied through a sound loudness tolerance level analyzer 212 where sound loudness tolerance level analysis takes place (FD). The sound loudness tolerance level analysis involves examining the loudness of the modified audio signal and comparing it with the user's sound loudness tolerance level at each audiometric frequency in accordance with the stored individualized audiological profile. If the loudness level at a specific frequency is greater than the user's sound loudness tolerance level, the system will adjust the loudness accordingly (FE). With the completion of the tolerance level analysis, the system converts the adjusted frequency-domain audio signal back to its equivalent time-domain audio signal in an inverse Fourier transform module 214 (FF) to produce the desired enhanced audio signals to be played as enhanced audio. Any loudness caution signal provided to the user can then be released.

In one embodiment of this invention, the system 10 refers to the uncomfortable loudness level as the sound loudness tolerance level, and to hearing loss as the type of hearing impairment being considered.

In another embodiment of this invention, the system 10 further refers to tinnitus pitch, tinnitus sensation level, tinnitus minimum audible level, and tinnitus UCL as the sound loudness tolerance level and hearing loss with tinnitus as the type of hearing impairment being considered.

The system 10 provides both automatic and manual gain adjustment options to the user where the automatic gain adjustment option is triggered by the acoustic environment and the manual gain adjustment option is user triggered.

In one embodiment of the invention, the system 10 begins to function with initiating the acoustic environment frequency composition analysis. The system automatically captures and analyzes the frequency composition in the current acoustic environment and creates an updated environment profile on a scheduled basis, oftentimes at every 50 ms. The system then uses the updated environment profile characteristics to automatically determine the amount of gain needed to allow the user to comfortably hear as desired and comprehend the enhanced audio without suffering any new or advanced ear damage.

In another embodiment of the invention, the system 10 provides the user with multiple gain adjustment options. The user may dynamically adjust the amount of gain needed to sufficiently hear and comprehend enhanced audio as governed by the sound enhancement process in various circumstances.

In another embodiment of the invention, the environment profiles generated are stored in a data repository along with the identification information on the environments associated with the environment profiles. The stored environment profiles can be accessed for future repeated use when the system encounters the same environment. In one embodiment, the environment identification information is the Global Positioning System (GPS) coordinates of the locations where the environment profiles are generated. As such, the environment profile for a particular environment can be identified and retrieved from the data repository for use based on a GPS coordinate detected by the system. In another embodiment, the environment identification information can be the time of the day, day of the week, week of the month, month of the year, and/or season of the year during which the environment profile is generated. As such, the environment profile for a particular environment can be identified and retrieved from the data repository based on the present time of the day, day of the week, week of the month, month of the year and/or season of the year when the system is being used.

In summary, this software-based system automates the enhancement process of audio from a computerized apparatus to complement a user's unique audio hearing characteristics based upon the user's individualized audiological profile. The individualized audiological profile can be obtained through either a self-administered hearing test or a professionally administered hearing test. The self-administered hearing test refers to profiles created from a computerized apparatus. This approach performs a capturing process on each ear and includes taking a hearing test, a UCL test, a most comfort level (MCL) test and/or a tinnitus matching test. Not all of these tests are necessary to use the system 10 and are considered optional. The system saves the individualized audiological profile on the local hearing enhancement apparatus and/or submits a copy to a data repository. The professionally administered test refers to profiles compiled from data provided by an appropriate healthcare professional. As outlined below, the data from a professionally administered test includes a pure tone audiogram, UCL and MCL test results for each audiometric frequency and tinnitus characteristic. The healthcare professional may enter the data on a suitably enabled apparatus or through the Internet into the web-accessed data repository.

A software-based system according to certain embodiments of the invention will advantageously have the capability to accept any parameters from a professionally produced audiogram. Such parameters include, according to standard designations in the art: Among the conventional tests are AC Unmasked or Masked, BC Unmasked or Masked, BC Forehead Unmasked or Masked, PTA, MCL, UCL, SRT Speech Discrimination, and Audio Source used in the Speech Reception Threshold (SRT) and Speech Discrimination Tests, i.e., sound clips on CD or tape, or computer generated sound clips for both the left and right ears at the following frequencies:

Hearing Level in dB at 125 Hz
Hearing Level in dB at 250 Hz
Hearing Level in dB at 500 Hz
Hearing Level in dB at 1 kHz
Hearing Level in dB at 2 kHz
Hearing Level in dB at 3 kHz
Hearing Level in dB at 4 kHz
Hearing Level in dB at 6 kHz
Hearing Level in dB at 8 kHz By default, the system bases its sound enhancement process on the most recent individualized audiological profile. During operation, the system compares the most recent individualized audiological profile to those on the local apparatus and the data repository. If the one stored in data repository 26 is more current, it will overwrite the local version (unless otherwise configured). If the profile on the local apparatus is more current, the system uploads the local profile to the data repository. In the absence of Internet connectivity, the system will use the local profile for the sound enhancement process. The date and time comparison process is typically performed daily with frequent monitoring for profile changes on the local apparatus. Whenever the system detects changes, it recalculates the gains and performs the sound enhancement with the updated data.

Referring to the following paragraphs, a sample implementation of Custom Enhanced Sound (CES), also known as the ACEHearing process, according to [BKL1] the invention is presented as a series of pseudo-code listings. To enhance clarity of this pseudo-code, there is no attempt at succinctness through use of language-specific statements that are common in certain programming languages, such as, Java. The intent here is to employ generic statements whose interpretation will be obvious to those of normal skill in software programming.

```
enable CESound(Boolean enable) {
/**
If the user is turning CESound off, then disable all filters
*/
   if (enable == false) {
   disableAllFilters( );
   return;
   }
/**
* If the user is turning CESound on, then perform the following:
* - get the user's audiological profile
```

```
* - calculate the proper filter coefficients based on the current algorithm
* - generate input filters (for use with the capturing device(s), such as
microphone or sound card input
* - generate the output filters (for use with the output device(s), such as
the speaker or headphone)
* - apply the input filters to the capturing device(s)
* - apply the output filters to the output device(s)
*/
    UserProfile userProfile = getUserProfile( );
    FilterCoefficients filterCoefficients =
    calculateFilterCoefficients(userProfile);
    Array inputFilters = generateInputFilters(filterCoefficients);
    Array outputFilters = generateOutputFilters(filterCoefficients);
    applyFilters(inputSource, inputFilters);
    applyFilters(outputDevice, outputFilters);
    UserProfile get UserProfile( ) {
    UserProfile userProfile = new UserProfile( ); // the UserProfile object
       to be returned
/*
* If able to connect to the central database at the remote data repository,
then synch with it to ascertain whether we have the most current active
user profile for the user
*/
if (connectToCentralDatabase( ) = true) {
User user = getCurrentUser( );
userProfile = syncUserProfile(user);
} else {
/*
* If unable to connect to the central database, then use the
* latest active user profile in the local database on the device
*/
userProfile = getLocalUserProfile( );
}
return userProfile;
}
perform HearingTest( ) {
UserProfile userProfile = new UserProfile( );
performMinimumAudibleLevelTest(userProfile);
performMostUncomfortableLevelTest(userProfile);
if (modelDialogAsk("Would you like to perform Tinnitus Matching?")) {
performTinnitusMatchingTest(userProfile);
}
acquireUserInformation( );
saveToLocalDatabase(userProfile);
saveToCentralDatabase(userProfile);
}
perform MimimalAudibleLevelTest(UserProfile userProfile){
userProfile.setMALRight1000(RIGHT_EAR,1000);
userProfile.setMALRight2000(RIGHT_EAR,2000);
userProfile.setMALRight4000(RIGHT_EAR,4000);
userProfile.setMALRight8000(RIGHT_EAR,8000);
userProfile.setMALRight250(RIGHT_EAR,250);
userProfile.setMALRight500(RIGHT_EAR,500);
userProfile.setMALLeft1000(LEFT_EAR,1000);
userProfile.setMALLeft2000(LEFT_EAR,2000);
userProfile.setMALLeft4000(LEFT_EAR,4000);
userProfile.setMALLeft8000(LEFT_EAR,8000);
userProfile.setMALLeft250(LEFT_EAR,250);
userProfile.setMALLeft500(LEFT_EAR,500);
}
perform MostUncomforableLevelTest(UserProfile userProfile){
userProfile.setMALRight1000(RIGHT_EAR,1000);
userProfile.setMALRight2000(RIGHT_EAR,2000);
userProfile.setMALRight4000(RIGHT_EAR,4000);
userProfile.setMALRight8000(RIGHT_EAR,8000);
userProfile.setMALRight250(RIGHT_EAR,250);
userProfile.setMALRight500(RIGHT_EAR,500);
userProfile.setMALLeft1000(LEFT_EAR,1000);
userProfile.setMALLeft2000(LEFT_EAR,2000);
userProfile.setMALLeft4000(LEFT_EAR,4000);
userProfile.setMALLeft8000(LEFT_EAR,8000);
userProfile.setMALLeft250(LEFT_EAR,250);
userProfile.setMALLeft500(LEFT_EAR, 500)
}
int saveToCentralDatabase(UserProfile userProfile) {
if ( openConnectionToCentralDatabase( ) == false){
return CONNECTION_FAILED;
}
int returnCode= updateProfileToCentralDatabase(userProfile);
closeConnectionToCentralDatabase( );
return returnCode;
}
```

Although the preceding embodiments of the invention have been described generally in the context of hearing profiles for individual users being isolated from device and environmental factors, other systems and methods of the invention make advantageous use of a shaped "auditory profile" that only applies to a particular signal pathway that has been measured, in the environment in which it was measured. Thus, a system and method will now be described which establishes a relationship between the electronic signal in a device and a user's auditory perception of the sound generated from the device in any environment; captures (profiles) the data set (termed or described as the "auditory profile") that represents the established relationship between the user's auditory perception and the electronic signal in a device under any chosen environment; and processes the electrical audio signals according to the selected "auditory profile" and a set of applied rules, parameters and algorithms; whereby the electrical audio signals are adjusted for the characteristics of the electronic components in a device and the user's auditory perception in any environment with the aim of providing an optimized full audio experience.

1. Acquiring the "Auditory Profile"

In one embodiment, with reference to FIGS. 16-19, 21, and 22, the user, via a graphical user interface, is asked to identify multiple reference points over a range of frequencies (these may be as few as two different frequencies) at which the sound output levels are at their minimum audible level. The system first presents to the user a sound signal of a particular frequency. The loudness adjustment could be done via a tool, such as a slider, a knob or a volume rocker, or voice commands, or even eye movements. The user adjusts the loudness until he or she can barely hear the signal. The user sets the reference point at the lowest audible level and then proceeds with the next setting at a different frequency. In this manner, each reference point takes into consideration the inherent specifications of the device (such as circuitry and transducer characteristics), the positioning of the device (such as the fit of earphones), the environment in which the identification takes place, the anatomic characteristics of the user's ear canal and ear drum, and the user's hearing capabilities.

When the user has successfully located the first reference point, the system saves it and repeats the process at another frequency. It is important to note that the reference points collected throughout the process do not reflect a person's auditory threshold of hearing as traditionally viewed in a professional hearing test context. They are points at which the user can barely hear the audio signals with reference to the testing device and its specifications, positioning of the device in relation to the ear, the environment in which the identification took place, and the anatomic characteristics of the ear canal, ear drum and hearing pathway. The saved reference points (which may be as few as two per ear) are termed as the person's "auditory profile" under those circumstances. Thus, a user may have multiple "auditory profiles" for different devices, choice of ear phones and/or listening environments. This "auditory profile" only applies to the signal path that has been measured (which comprises not only the user's hearing characteristics but also other factors including the device's signal, circuit, and transducer/ ear bud or ear phone; whether the device fits onto or into the ear; the anatomy of the user's ear canal; and the environment). The captured "auditory profile" thus combines together the device's transducer characteristics and the user's hearing perception into one relationship. Significantly, without the need to assess whether any part of the profile is attributable to hearing loss, the system can use this "auditory profile" to determine the sound enhancement needed to compensate for the frequency response characteristics of the user's auditory perception under the particular circumstances of the measured signal path.

By not relying on measuring true hearing threshold levels, but rather only establishing a relationship that provides the "shape" of a profile for a particular complete pathway, the approach according to this aspect of the invention is distinguished from traditional hearing testing and enhancement of audio using the hearing aid principles. So the "auditory profile" is not the individual user's hearing profile where thresholds have been measured in a sound proof or quiet environment, but an "auditory profile" in the form of a data set that represents a relationship created between the signal produced by any device (that takes into consideration the device's circuitry and its transducer or with the particular ear bud chosen by the user and its fitting into the ear canal), to the user's audibility thresholds for that particular device in any chosen environment. So, the "auditory profile" (or data set used as a platform upon which to enhance a sound signal) "belongs" or relates to the specific circuit and its user under the conditions in which it was established. As stated above, this "auditory profile" only applies to the measured signal path. Different "auditory profiles" can be acquired by an individual (or even a number of users on the same device) for different circumstances (ear bud and/or environment changes) and stored in the device for appropriate use.

In another embodiment, the auditory profile also takes into consideration both ears of the users. In the aforementioned auditory profile acquisition procedure may take the hearing profile from each of the left and right ear one at a time. However, the system takes into account that a person's perception of loudness is not absolute, the loudness difference between the left and right ears could affect the person on the perception of balance of sound volume. In this case, the system, instead of computing the sound enhancement responses separately for the left and right ears, computes the sound enhancement responses with the left and right ears' hearing profiles combined with consideration of gain boundaries to achieve better balance, audio quality, and an increase in the dynamic range of the modified audio signal.

To illustrate using an example, a user's auditory profile acquired may lead to a desired sound enhancement response having a gain of 5 dB at 250 Hz for her right ear; 20 dB at 12500 Hz for both ears; and 10 dB at all other frequencies for both ears. In this example, the system takes the lowest gain, which is 5 dB, and subtract from all the gains; thus, the final sound enhancement response will be 0 dB at 250 Hz for the right ear; 15 dB at 12500 Hz for both ears; and 5 dB at all other frequencies for both ears. The overall effect is that the dynamic range is increased while keeping the balance of the left and right ears. In another embodiment, all the gains in the desired sound enhancement response for both ears may be reduced a fraction or percentage of the lowest gain.

The system proceeds in capturing and storing the "auditory profile" in the form of data.

2. User Preferences

The "auditory profile" is then selected (from one or any number of stored profiles) by the user to be the preferred "auditory profile" for customization/enhancement by the device according to the user's preference which would logically be based on the choice of listening device and/or environmental circumstance.

Alternatively, selection of a best-fit auditory profile from a plurality of stored profiles may be performed automatically based on sampling or detection of characteristics or components of the signal pathway through which enhanced audio is to be transmitted to the individual. Features of the signal pathway that may be automatically sampled or detected may include, without limitation, environmental sounds (for example, their overall intensity, tonality/atonality, and/or frequency-specific intensity), an identifying signature and/or measured auditory characteristics (such as frequency response) of the transducer in use; the position, angular orientation, or movements of the transducer (including such as would indicate in or on which of an individual's ears the transducer is positioned); and any contact, touch, or pressure on the transducer, especially by a user's ear, such as would indicate proximity, or in the case of a transducer inserted in the ear canal, snugness of fit. Automatic selection may also be partially user-controlled, for example by prompting the user to specify the relative importance of different features of the signal pathway to the automatic selection. Thus, in one simple example, the user may request the device to select the profile having the closest environmental sound conditions to the sound conditions present at the time of enhanced audio transmission. In this example, it may be particularly advantageous for a large number of audio profiles to be stored, corresponding to a large number of different environmental soundscapes, given the wide range of variability possible for background sound conditions.

Additionally, the user may be advantageously enabled at any subsequent time to apply and select additional personal preferences, for example, diminishing high tones and/or boosting low tones. This add-on feature may synergize with automatic best-fit profile identification. For example, if and when the system automatically selects a best-fit profile based on sampled or detected conditions, followed by the user making a prompt manual adjustment of an overall volume or frequency-specific volume, the manual adjustment may be fed back into the system to train the automatic profile selection algorithm in accordance with machine-learning principles.

Figure 28:
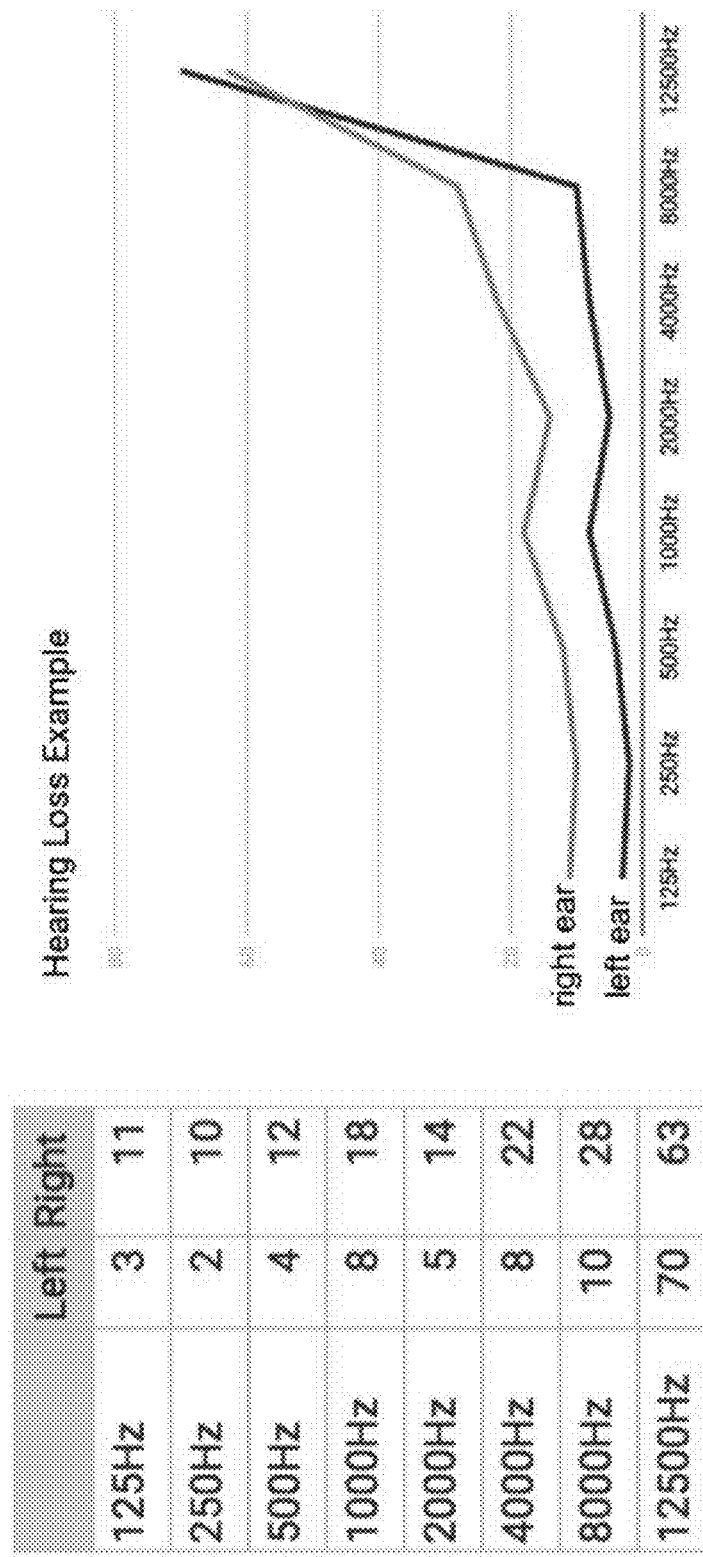
FIG. 28 illustrates an exemplary hearing profile showing high sensitivity except at the frequency of 12500 Hz for both ears.
Figure 29:
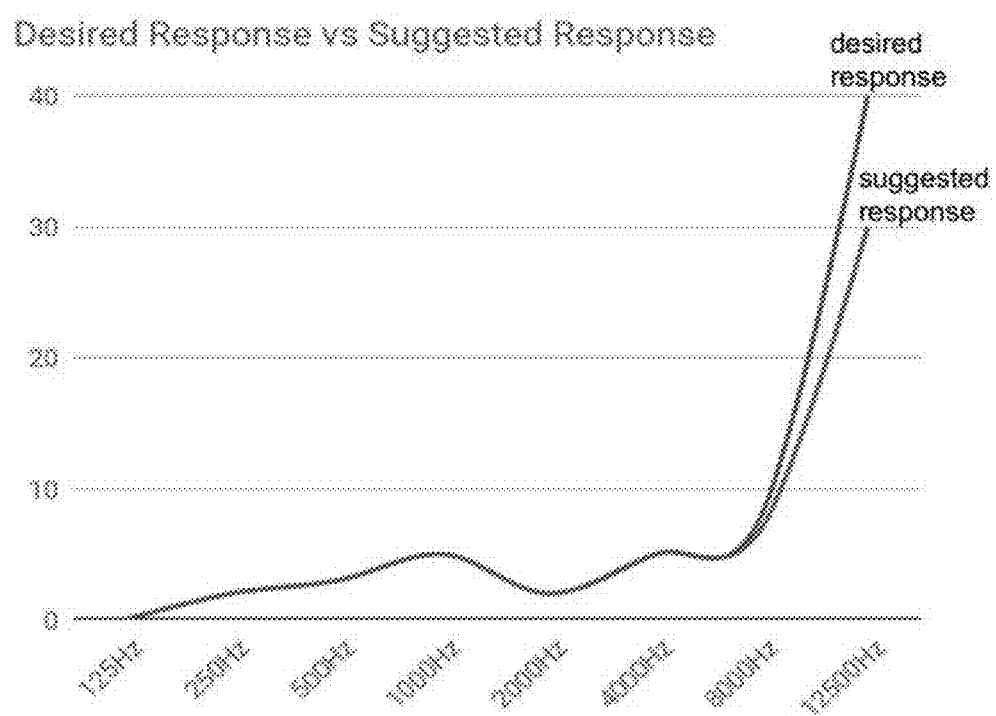
FIG. 29 shows an exemplary desired sound enhancement response for an exemplary auditory profile detected to be fitting in a pattern associated with a manual volume lowering versus a suggested response in accordance to another aspect of the present invention.

In accordance to another aspect of the present invention, the aforementioned user's manual adjustments of an overall volume or frequency-specific volume that are to be fed back into the system are not only used in training the automatic profile selection algorithm, but also form a feedback loop in adjusting the user's auditory profiles and the auditory profiles of other users of the system stored in the data repository as well. For example, a user may have a hearing profile showing high sensitivity except at the frequency of 12500 Hz for both ears, as illustrated in the frequency response chart depicted in FIG. 28. In this case, the sound enhancement response would be to amplify at the frequencies around 12500 Hz only, and about 30 dB more than other frequencies. However, when the system receives from the user and/or other users multiple instances of manual adjustments to adjust down (or up) the 12500 Hz amplification, the system detects whether a pattern exists in accordance with machine-learning principles. In essence, a pattern is detected when the system finds two or more audiological profiles that are approximately same in shape and are associated with approximately the same manual gain adjustments. If such pattern is detected, for example multiple cases of manual volume lowering associated with auditory profiles having amplification of over 30 dB at around 12500 Hz and amplification of maximum 10 dB at all other frequencies, the system will suggest an alternative sound enhancement response when the selection of similar auditory profile is made. For example, FIG. 29 shows the desired sound enhancement response for a selected auditory profile that the system has detected to be fitting in a pattern associated with a manual volume lowering versus a suggested response.

Alternatively or additionally, in response to the manual adjustment, the system may prompt the user to select whether to store a new profile associating the active signal enhancement settings, as manually modified, with the sampled environmental soundscape. In one embodiment, the system may decide whether to apply a training adjustment to its automatic selection algorithm, and/or to invite the user to store a new profile, based on some measured degree of difference between the sampled conditions and the stored conditions that were automatically selected as most resembling the sampled conditions. For example, if the difference is great, the system may only invite the user to store a new profile, as the manual adjustment may have been needed not because of a flaw in the automatic selection, but because the range of available stored profiles was insufficiently robust. Affirmative user responses to such prompting will help to populate the system with a critical mass of different stored profiles, thus refining its ability to optimize the user's listening experience over a wide range of different background soundscapes.

On the other hand, if the difference between the sampled condition and the stored condition is small, the system may only make a training adjustment to its selection algorithm. Alternatively, in some cases the system may base its corrective action, in whole or in part, on the user's response to the invitation to store a new profile. Thus, for example, if the user elects not to store a new profile, the system may apply a training adjustment to its algorithm, either in all cases of user refusal, or only if the user refuses the option to create a new profile and the difference between the sampled condition and the stored condition is below a certain limit. The threshold degree of difference above which the system will not correct its selection algorithm, regardless of user refusal to create the new profile, may be higher than the threshold degree of difference above which the system will invite the user to create a new profile.

Figure 30:
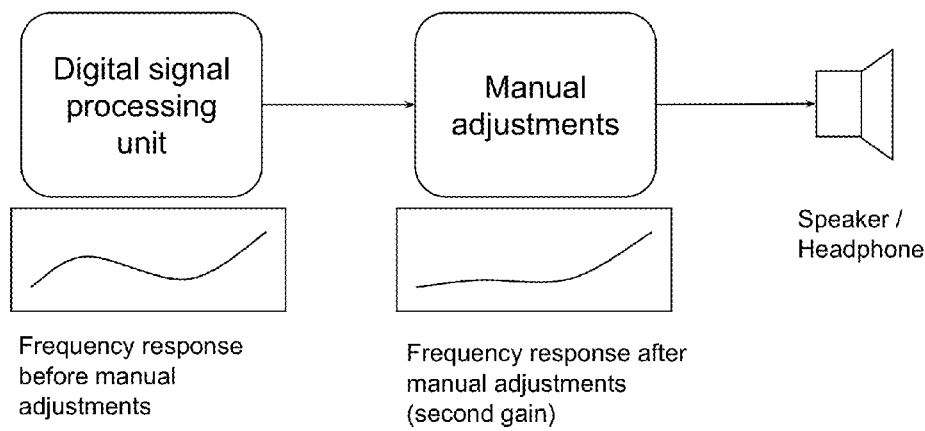
FIG. 30 illustrates a manual gain adjustment after a sound enhancement/modification in accordance to another aspect of the present invention.
Figure 31:
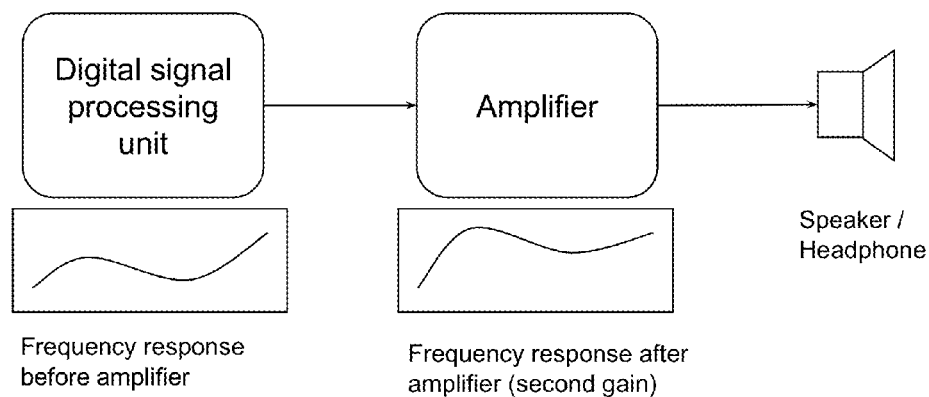
FIG. 31 illustrates a second gain adjustment after a sound enhancement/modification in accordance to another aspect of the present invention.

The aforesaid manual adjustment by the user post sound enhancement/modification based on the user's auditory profile may be regarded as a (second) gain adjustment to the enhanced/modified audio signal. This is illustrated in FIG. 30. Besides manually input by the user during runtime, this second gain adjustment can be pre-configured and/or automatically determined by the system. In general, this second gain adjustment can be, without limitation, a gain adjustment to prevent signal clipping; a gain 'shape' specific to the make, brand, and/or model of the sound equipment, transducer, and/or ear bud in the signal pathway; a gain 'shape' specific to individual's taste; and a gain 'shape' specific to type (e.g. genre) of sound/music. Further, this second gain adjustment can be, without limitation, performed as part of the sound enhancement/modification based on the user's auditory profile by the same processing component or circuitries, or separately after the sound enhancement/modification by a separate component or system (e.g. a standalone amplifier, transducer, earphone, or ear bud). The latter embodiment is illustrated in FIG. 31.

3. Runtime Factors

Figure 19:
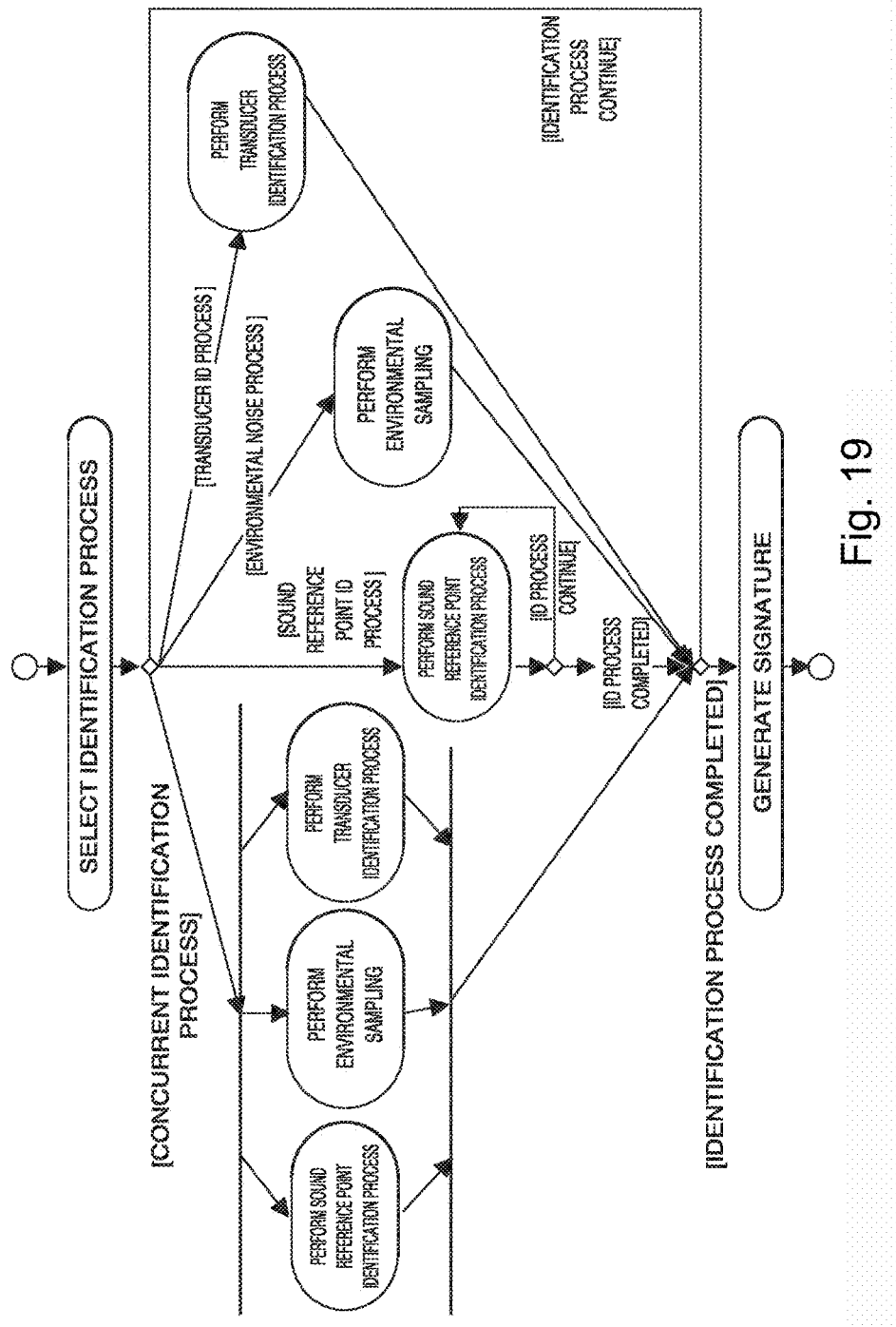
FIG. 19 is a flow chart illustrating a signature (shaped auditory profile) creation process according to an aspect of the invention.

With reference to FIG. 19, the selected "auditory profile" data set then determines a set of "parameters." These parameters are based upon rules applied on how to treat the data taking into account one or a number of factors, e.g., i) factor for dB level measured at each reference point, ii) factor for environment noise measured, and iii) factor for known transducer characteristics. Then, according to the pre-selected "auditory profile" and applicable rules, parameters and algorithms, the device's electrical signals are subjected to processing to compensate for the inherent frequency response characteristics of the user's auditory perception and electronic components in the device, under the environment in which the selected "auditory profile" was generated, referring to FIG. 18.

Signal processing may or may not be guided by the device detecting differences between stored test conditions and conditions measured concurrently with the signal processing. For example, if the differences between the test conditions associated with a manually selected profile and the current listening environment are large, the system may alert the user to this fact and prompt the user to choose whether to create a new profile, similar to the process described above in conjunction with automatic profile selection followed by manual user adjustments. Alternatively, the system may analytically extrapolate a signal enhancement operation to be performed, by modifying the enhancement operation associated with the pre-selected profile to account for differences between the test conditions and presently detected conditions.

The flow is thus as follows: Hearing test protocol with or without environment noise measure auditory profile capture rules (how the profile is being used⇔parameters (produced by the rules⇔algorithms (how the parameters are used-⇔processing (signal⇔result).

The signals thus generated correct for the listener's hearing profile (which may or may not include effects of hearing impairment); correct for the sound or music the listener wants to hear (the listener is able to tune the auditory profile after trying some speech or music); correct for the unique features of the particular device upon which the profile was generated, e.g. a phone's (or other audio output device) transducer's frequency responses; correct for the energy transfer from the transducer to the eardrum, which depends on the listener's individual anatomy and preference for positioning the transducer; and correct for the sound environment in which the listener has created the auditory profile and will use the device.

In another embodiment, the system allows the user to select to introduce the sound enhancement gradually over the reproduction session of a song or sound clip, or over a period of time of usage of the particular device. The gradual introduction of the sound enhancement means that each of the gains in a desired response is added with increasing amplitude from an initial amplitude to its respective computed desired amplitude. The initial amplitude can be 0 dB or any amplitude lower than the computed desired amplitude of the gain.

Figure 20:
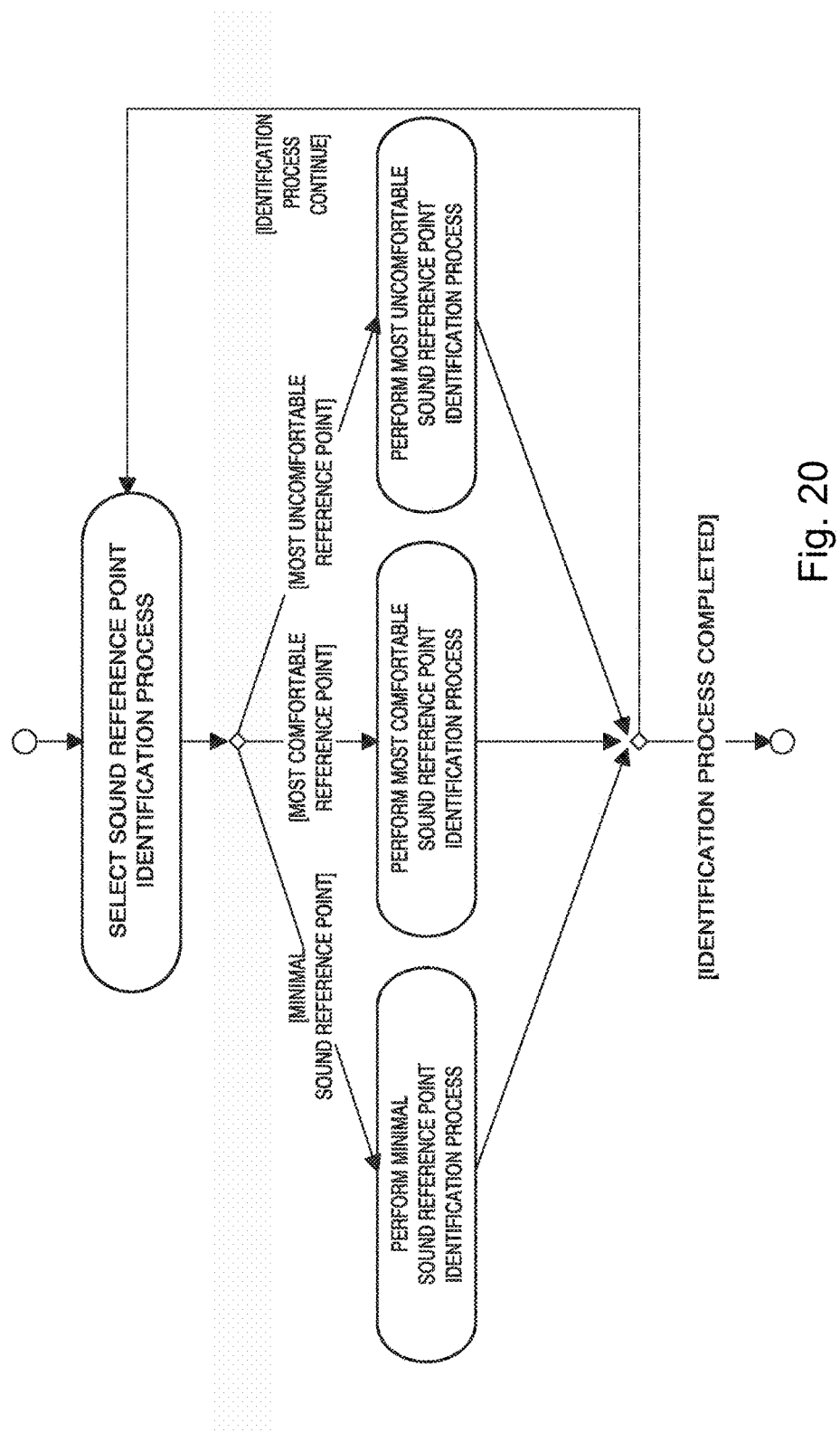
FIG. 20 is a flow chart illustrating a sound reference point identification process according to an aspect of the invention.
Figure 21:
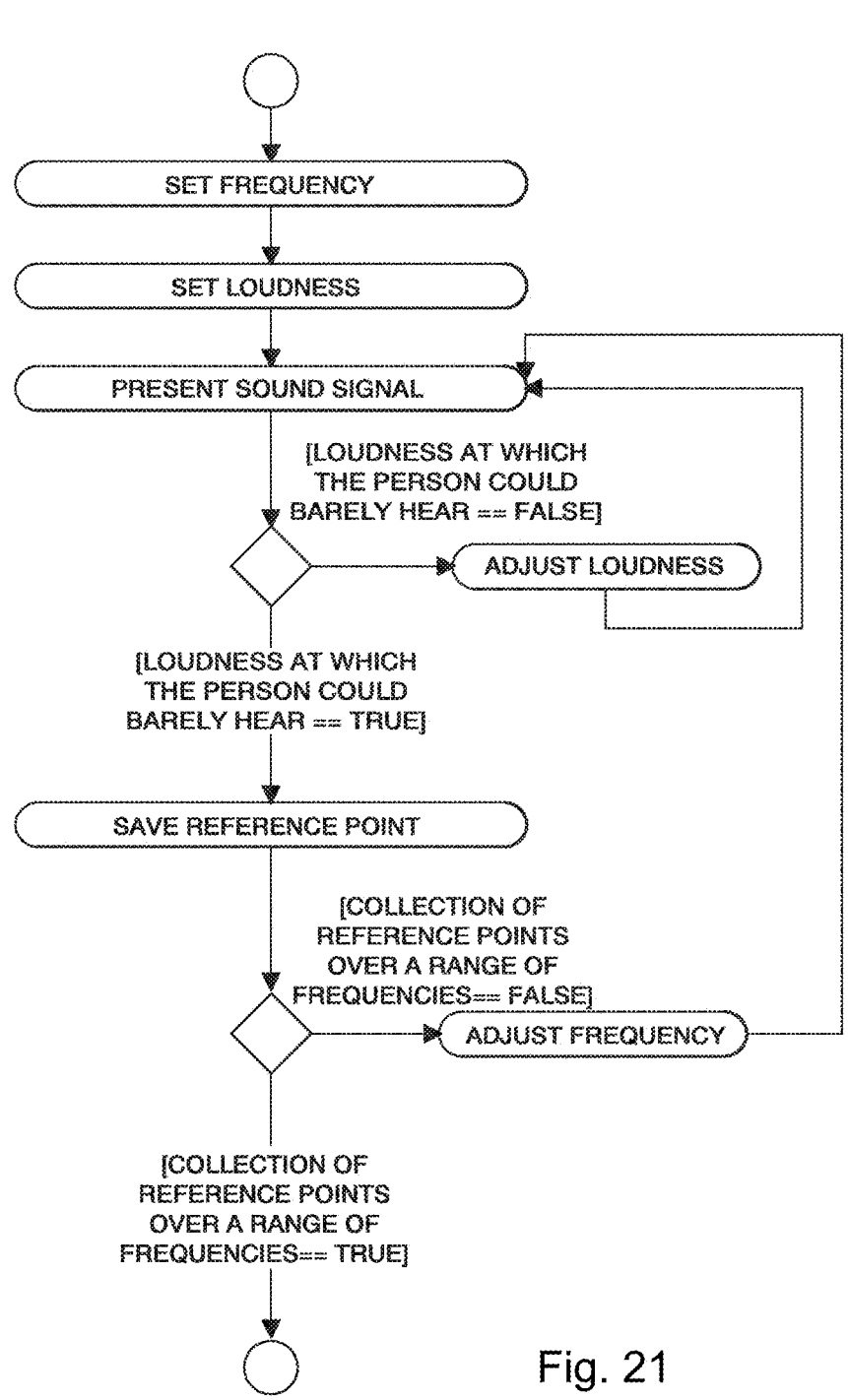
FIG. 21 is a flow chart illustrating a minimum sound reference point identification process according to an aspect of the invention.
Figure 22:
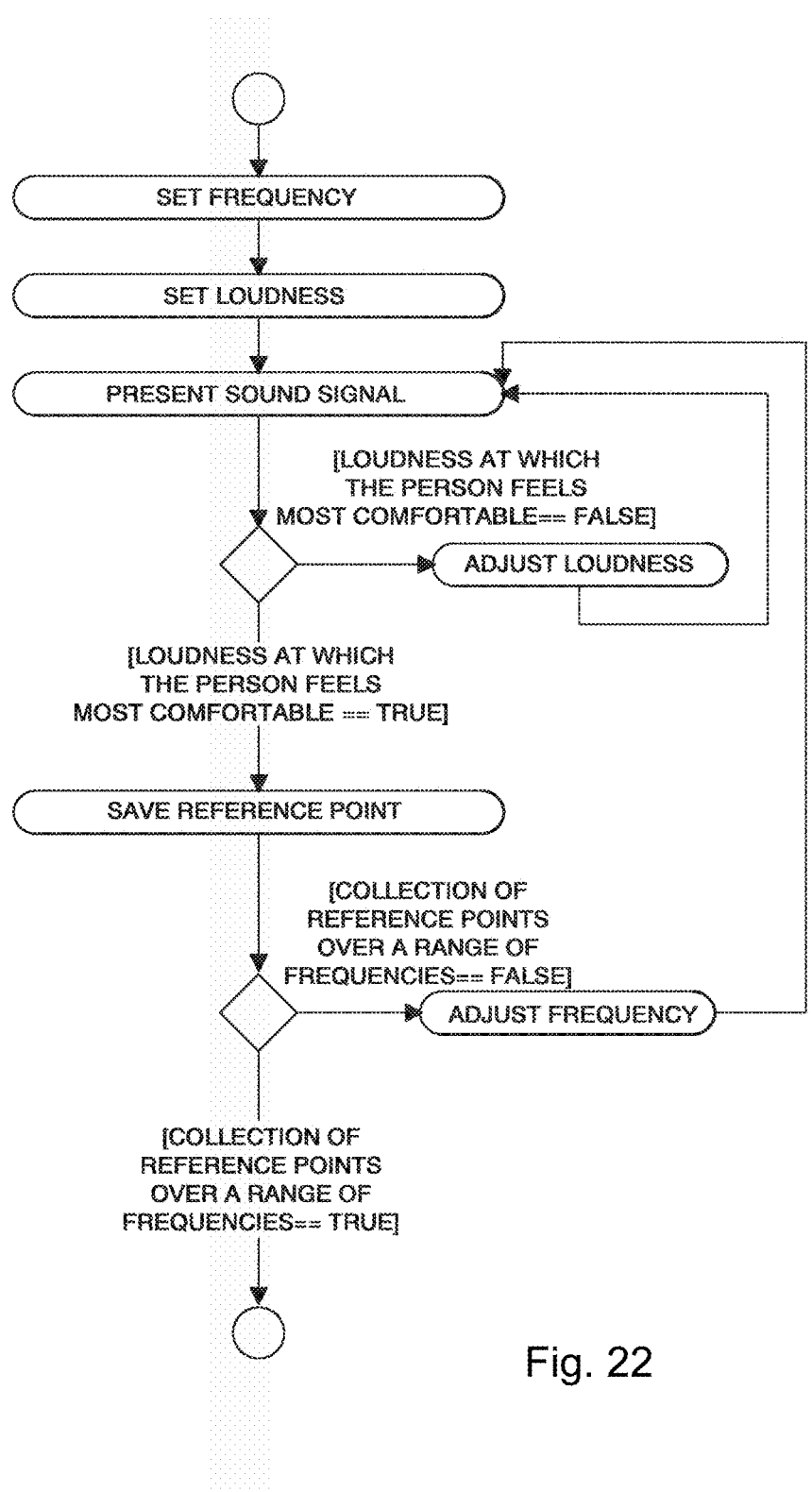
FIG. 22 is a flow chart illustrating a most comfortable sound reference point identification process according to an aspect of the invention.

In another embodiment, referring to FIGS. 20 and 22, the user, via a graphical user interface, is asked to identify multiple reference points in which the sound levels are at their most comfortable level over a range of frequencies.

Figure 23:
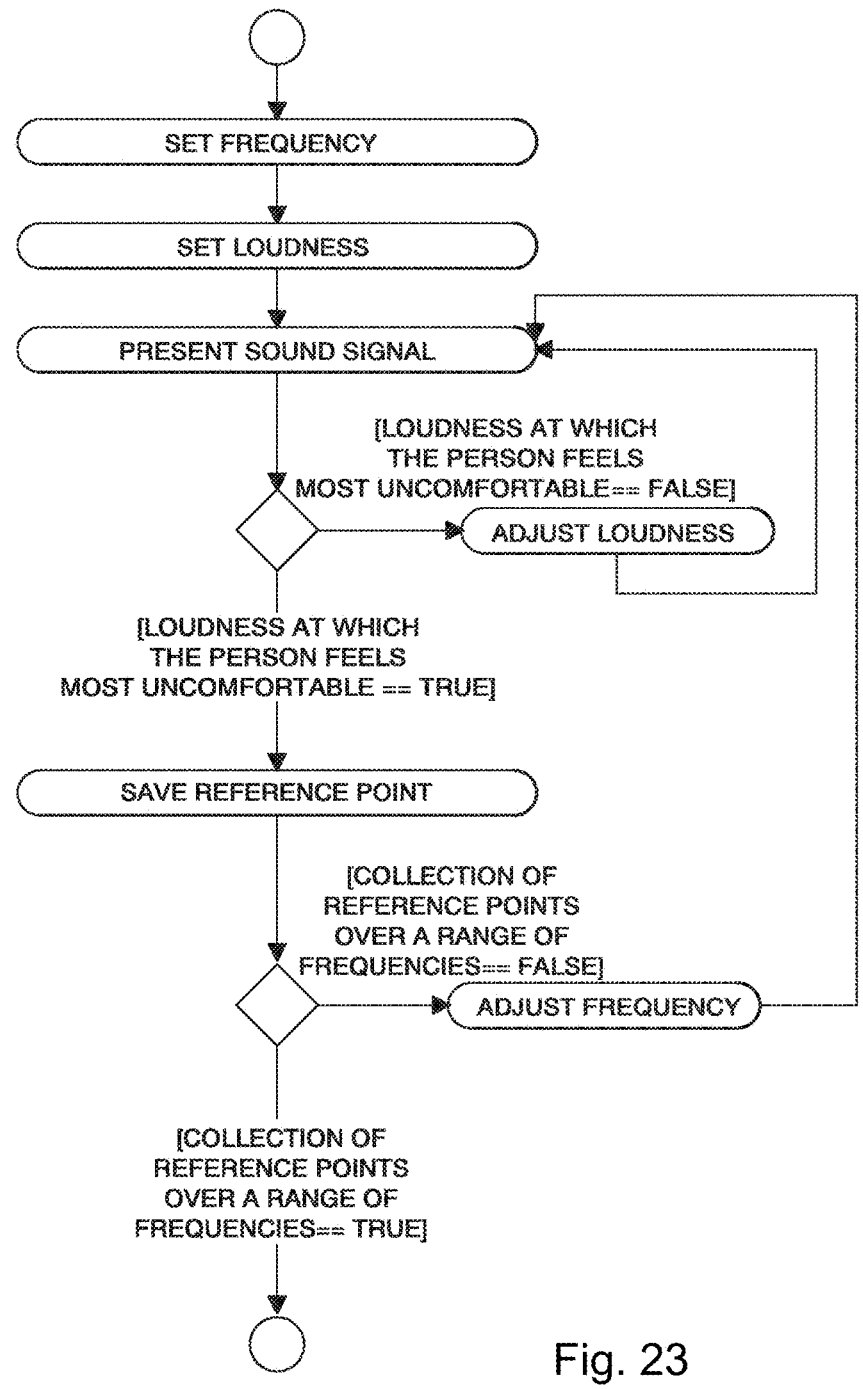
FIG. 23 is a flow chart illustrating an uncomfortable sound reference point identification process according to an aspect of the invention.

In yet another embodiment, with reference to FIGS. 20 and 23, the user, via a graphical user interface, is asked to identify multiple reference points at and above which the sound levels are uncomfortable over a range of frequencies.

In another embodiment, illustrated in FIG. 24, the user, via a graphical user interface, is asked to select an auditory profile from a list of existing auditory profiles.

In yet another embodiment, referring to FIGS. 24 and 25, the user, via a graphical user interface, is given a choice, either to create a new auditory profile from scratch or select one from a list of existing auditory profiles.

Figure 26:
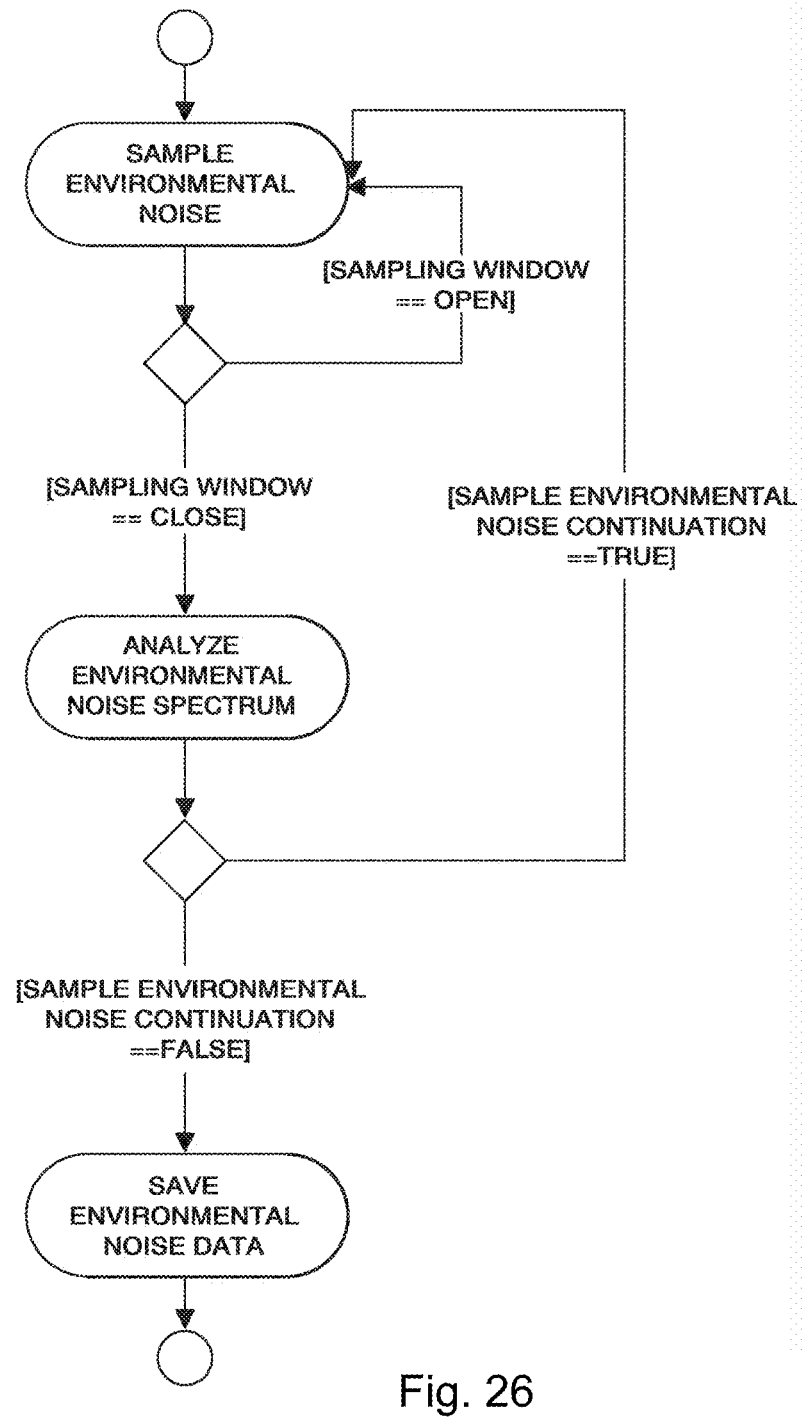
FIG. 26 is a flow chart illustrating an environmental sampling process according to an aspect of the invention.

In yet another embodiment, referring to FIG. 26, the system can be configured to sample, analyze and save environmental noise in the form of data, either at a user's initiation, via a graphical user interface, or automatically.

Figure 27:
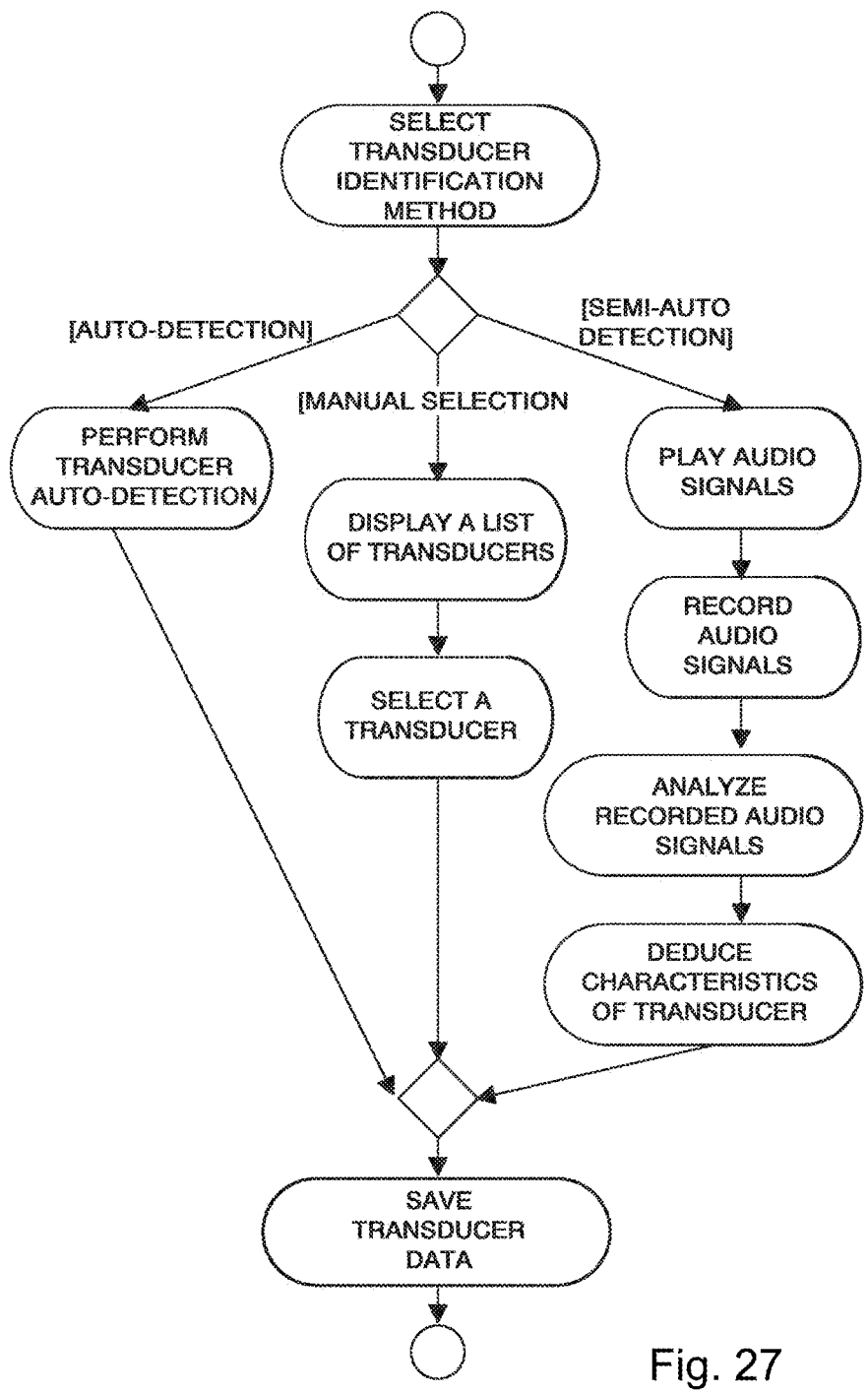
FIG. 27 is a flow chart illustrating a transducer identification process according to an aspect of the invention.

In yet another embodiment, illustrated in FIG. 27, the user, via a graphical user interface, is given a choice of indicating to the system an option of transducer identification mechanisms, being manual selection, semi-auto detection, or auto-detection of the brand/model of the earphone before undergoing the test protocol.

The invention has been explained with reference to specific embodiments. Other embodiments will be evident to those of ordinary skill in the art. Therefore, it is not intended that the invention be limited, except as indicated by the appended claims.

What is claimed is:

1. A method for reproducing sound to an individual using modified or enhanced audio signal tailored to audiological characteristics of the individual, comprising:
   capturing the individual's audio hearing characteristics, including determining the individual's minimum audible level for at least one audiometric frequency;
   analyzing the individual's hearing characteristics to generate an individualized audiological profile;
   storing the individualized audiological profile in a storage means;
   using the individualized audiological profile to determine a first frequency-specific gain adjustment for an input audio signal to compensate for frequency-dependent loudness deficits in the individual's hearing;
   generating a gradually modified audio signal by applying gradually the first gain adjustment to an input signal; and
   sound-reproducing from the gradually modified audio signal to the individual using an electronic device that reproduces sound;
   wherein the first gain adjustment comprises one or more first gains and each first gain having a desired first amplitude; and
   wherein the gradual application of the first gain adjustment to the input signal comprises applying each of the first gains with increasing amplitude from its respective initial first amplitude to its respective desired first amplitude to the input signal to generate the gradually modified audio signal; and
   wherein the initial first amplitude of each of the first gain is lower than its respective desired first amplitude.

2. The method of claim 1, wherein the gradual application of the first gain adjustment to an input signal to generate the gradually modified audio signal is performed over a sound-reproduction session.

3. The method of claim 1, wherein the gradual application of the first gain adjustment to an input signal to generate the gradually modified audio signal is performed over a period of time of usage of the electronic device.

4. The method of claim 1, further comprising:
   applying a second gain adjustment to convert the gradually modified audio signal to an enhanced audio signal; and
   sound-reproducing from the enhanced audio signal to the individual using the electronic device.

5. The method of claim 1, further comprising
   generating an environment profile including at least an environmental sound measurement;
   using the environment profile and the individualized audiological profile to determine the first gain adjustment;
   wherein the sound reproduction using the electronic device is in the environment profile.

6. The method of claim 5, further comprising periodically updating the environment profile during the sound-reproduction.

7. The method of claim 1, wherein said capturing the individual's audio hearing characteristics further comprising:
   capturing the audio hearing characteristics of the individual for a test signal pathway including:
      a transducer delivering the audio from the electronic device to the individual's ear, whether the transducer fits onto or into the individual's ear, the anatomy of the user's ear canal, and
      an environmental sound measurement;
   wherein the sound reproduction using the electronic device is through a listening signal pathway similar to the test signal pathway.

8. The method of claim 1, wherein the capturing of the individual's audio hearing characteristics comprises a self-administered test or a third party-administered test.

* * * * *